(12) United States Patent
Lamprich et al.

(10) Patent No.: US 7,862,617 B2
(45) Date of Patent: Jan. 4, 2011

(54) SPINAL DISC PROSTHESIS APPARATUS AND PLACEMENT METHOD

(75) Inventors: Lonnie Jay Lamprich, Oklahoma City, OK (US); Bradley Keith Lamprich, Oklahoma City, OK (US)

(73) Assignee: Lamprich Medical, LLC, Oklahoma City, OK (US)

( * ) Notice: Subject to any disclaimer, the term of this patent is extended or adjusted under 35 U.S.C. 154(b) by 1150 days.

(21) Appl. No.: 11/345,558

(22) Filed: Jan. 31, 2006

(65) Prior Publication Data

US 2006/0149382 A1 Jul. 6, 2006

Related U.S. Application Data

(63) Continuation-in-part of application No. 10/995,886, filed on Nov. 23, 2004, which is a continuation-in-part of application No. 10/899,898, filed on Jul. 27, 2004, now Pat. No. 7,172,628.

(51) Int. Cl.
*A61F 2/44* (2006.01)
(52) U.S. Cl. .................................... 623/17.16
(58) Field of Classification Search ... 623/17.11–17.16, 623/16.111; 606/191, 192
See application file for complete search history.

(56) References Cited

U.S. PATENT DOCUMENTS

| 4,772,287 A | * | 9/1988 | Ray et al. ................. 623/17.12 |
| 5,015,255 A | * | 5/1991 | Kuslich ....................... 128/898 |
| 5,059,193 A | | 10/1991 | Kuslich |
| 5,489,307 A | * | 2/1996 | Kuslich et al. ............... 128/898 |
| 5,549,679 A | | 8/1996 | Kuslich |
| 5,558,674 A | | 9/1996 | Heggeness et al. |
| 5,645,597 A | | 7/1997 | Krapiva |
| 5,674,295 A | | 10/1997 | Ray et al. |
| 5,772,661 A | | 6/1998 | Michelson |
| 5,865,846 A | | 2/1999 | Bryan et al. |
| 5,879,353 A | | 3/1999 | Terry |
| 5,928,284 A | | 7/1999 | Mehdizadeh |
| 5,991,997 A | | 11/1999 | Schley et al. |

(Continued)

FOREIGN PATENT DOCUMENTS

EP 0307241 3/1989

(Continued)

OTHER PUBLICATIONS

M. Neo et al., The Use of an Aiming Device in Posterior Atlantoaxial Transarticular Screw Fixation, 97 J. Neurosurg. 123 (Jul. 2002).

(Continued)

*Primary Examiner*—Alvin J. Stewart
(74) *Attorney, Agent, or Firm*—McAfee & Taft

(57) ABSTRACT

A spinal disc prosthesis and method of placing a spinal disc prosthesis between adjacent vertebrae are provided. The inventive spinal disc prosthesis can comprise one or more solid, compressible prosthesis elements that are formed prior to the method of placing the prosthesis, or one or more solid prosthesis elements that are formed in situ. The inventive method of placing a spinal disc prosthesis between adjacent vertebrae of a patient is based on a posterior approach. The invention also includes a spinal disc prosthesis insertion apparatus and specially constructed surgical instruments for use in carrying out the method.

27 Claims, 11 Drawing Sheets

U.S. PATENT DOCUMENTS

| | | | |
|---|---|---|---|
| 6,004,326 A * | 12/1999 | Castro et al. ................... 606/99 |
| 6,110,178 A | 8/2000 | Zech et al. |
| 6,231,609 B1 * | 5/2001 | Mehdizadeh ............. 623/17.11 |
| 6,261,311 B1 | 7/2001 | Sharkey et al. |
| 6,315,795 B1 | 11/2001 | Scarborough et al. |
| 6,368,350 B1 | 4/2002 | Erickson et al. |
| 6,402,785 B1 * | 6/2002 | Zdeblick et al. .......... 623/17.16 |
| 6,468,276 B1 | 10/2002 | McKay |
| 6,478,822 B1 | 11/2002 | Leroux et al. |
| 6,482,234 B1 | 11/2002 | Weber et al. |
| 6,537,279 B1 | 3/2003 | Michelson |
| 6,613,089 B1 | 9/2003 | Estes et al. |
| 6,695,851 B2 * | 2/2004 | Zdeblick et al. ............... 606/96 |
| 6,746,451 B2 | 6/2004 | Middleton et al. |
| 6,758,863 B2 | 7/2004 | Estes et al. |
| 6,764,514 B1 | 7/2004 | Li et al. |
| 2002/0045942 A1 | 4/2002 | Ham |
| 2003/0195520 A1 * | 10/2003 | Boyd et al. ................... 606/90 |
| 2004/0148028 A1 | 7/2004 | Ferree et al. |
| 2004/0153064 A1 | 8/2004 | Foley et al. |
| 2004/0215344 A1 | 10/2004 | Hochschuler et al. |
| 2005/0055099 A1 | 3/2005 | Ku |
| 2005/0059972 A1 | 3/2005 | Biscup |
| 2006/0030862 A1 | 2/2006 | De Villiers et al. |

FOREIGN PATENT DOCUMENTS

| | | |
|---|---|---|
| EP | 1 092 395 B1 | 4/2004 |
| WO | WO 2007/089858 A3 | 7/2008 |

OTHER PUBLICATIONS

Y. Ishida et al., Critical Analysis of Extensive Cervical Laminectomy, 24 Neurosurgery 215 (Feb. 1989).

B.L. Allen et al., The Biomechanics of Decompressive Laminectomy, 12 Spine 803 (Oct. 1987).

* cited by examiner

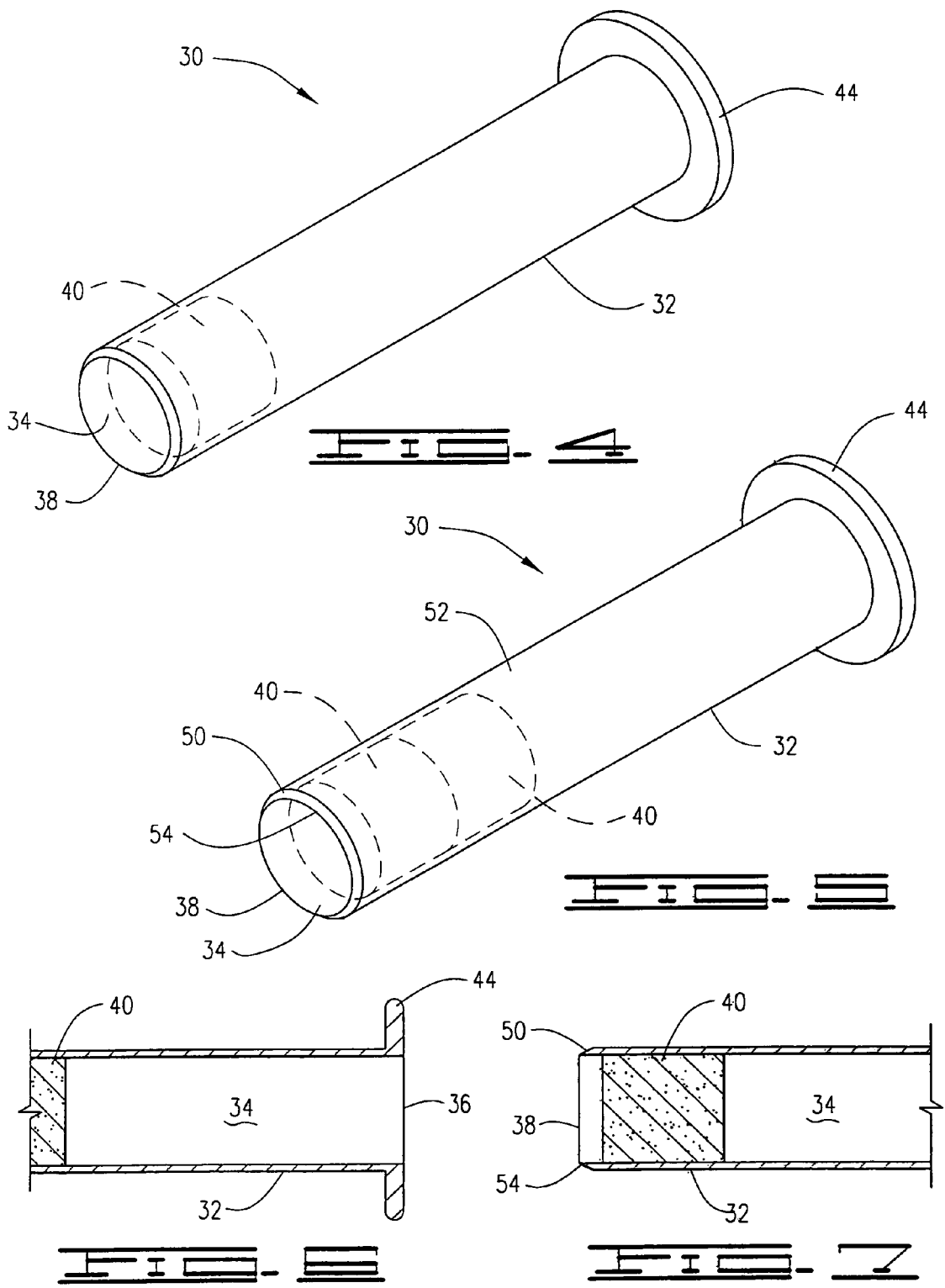

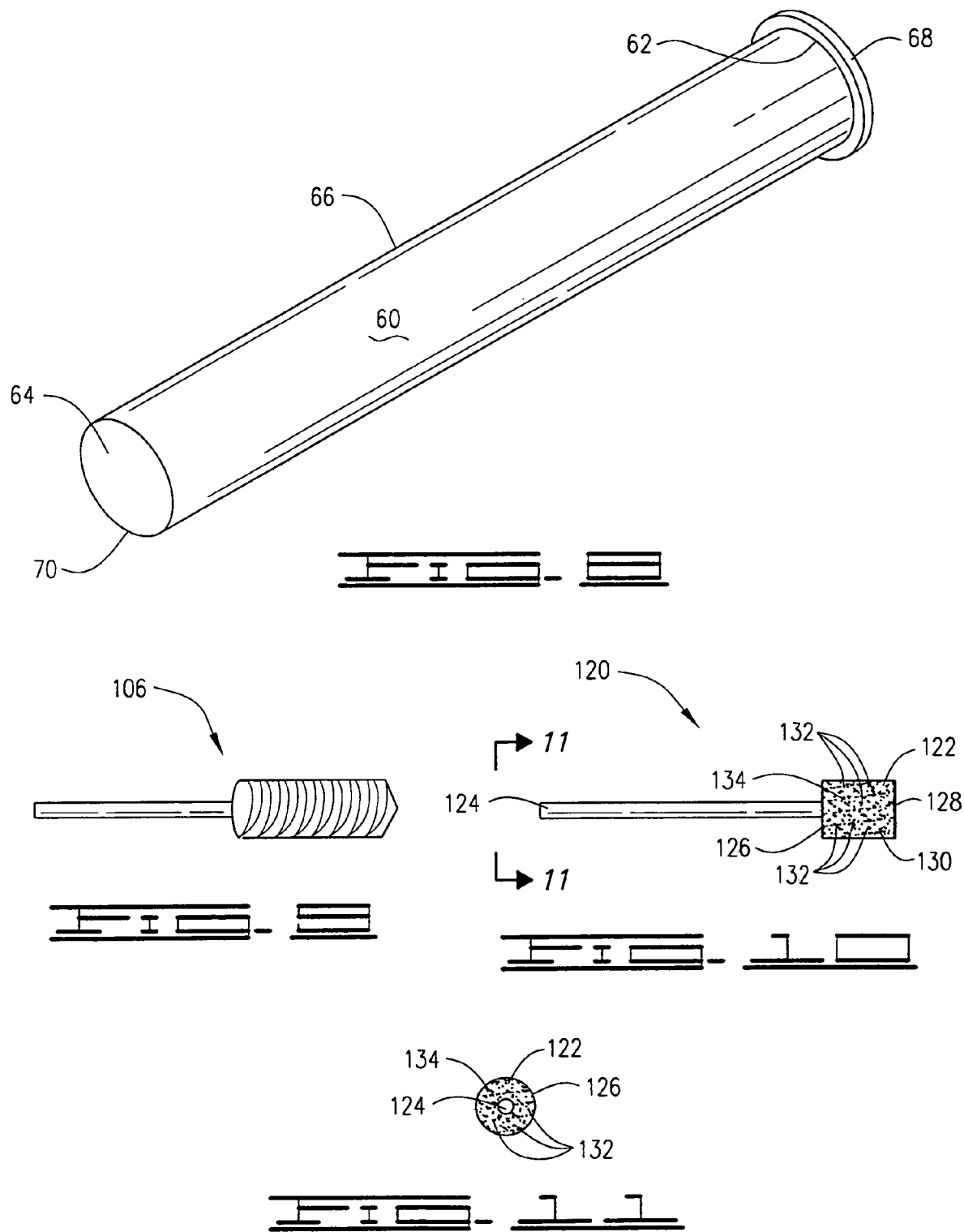

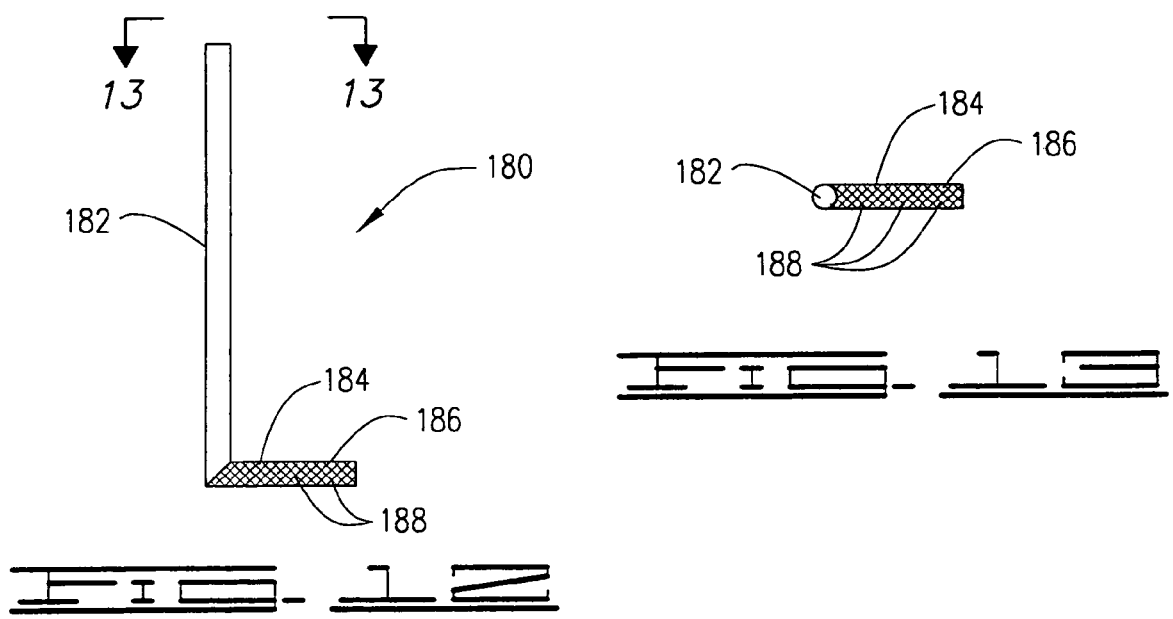
FIG. 12
FIG. 13
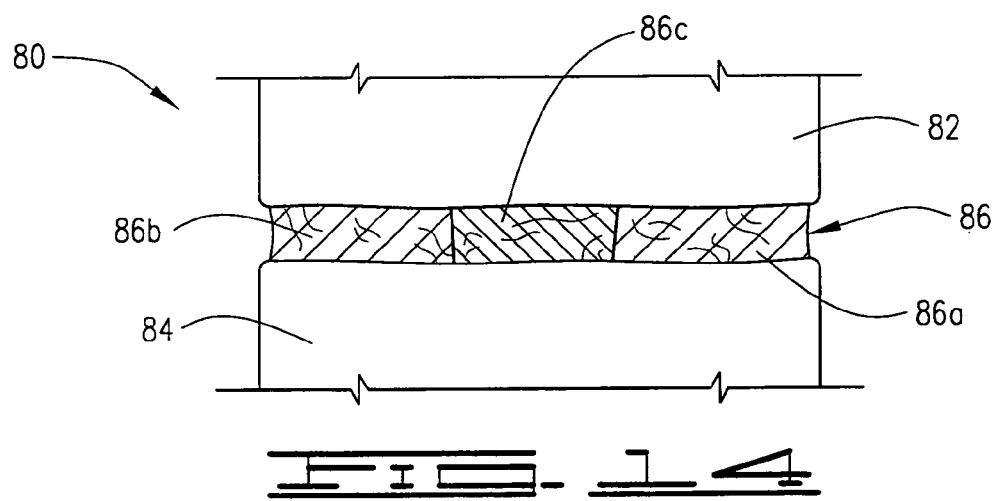
FIG. 14
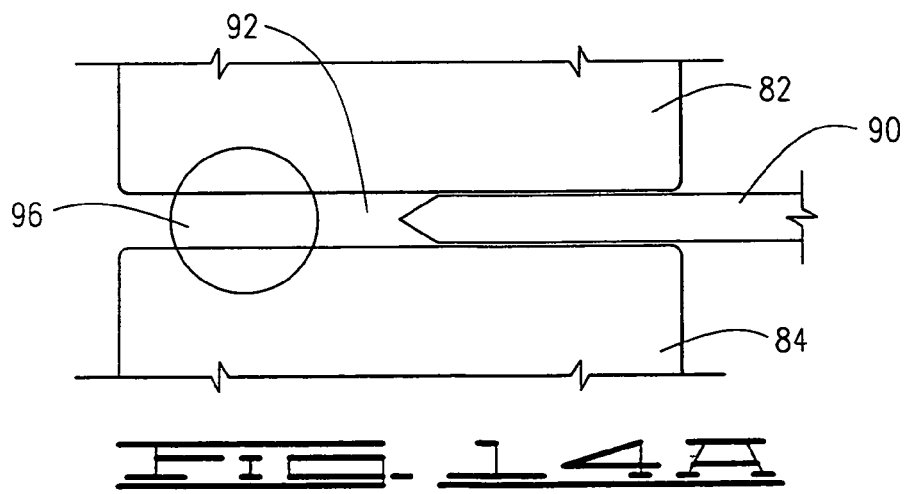
FIG. 14A

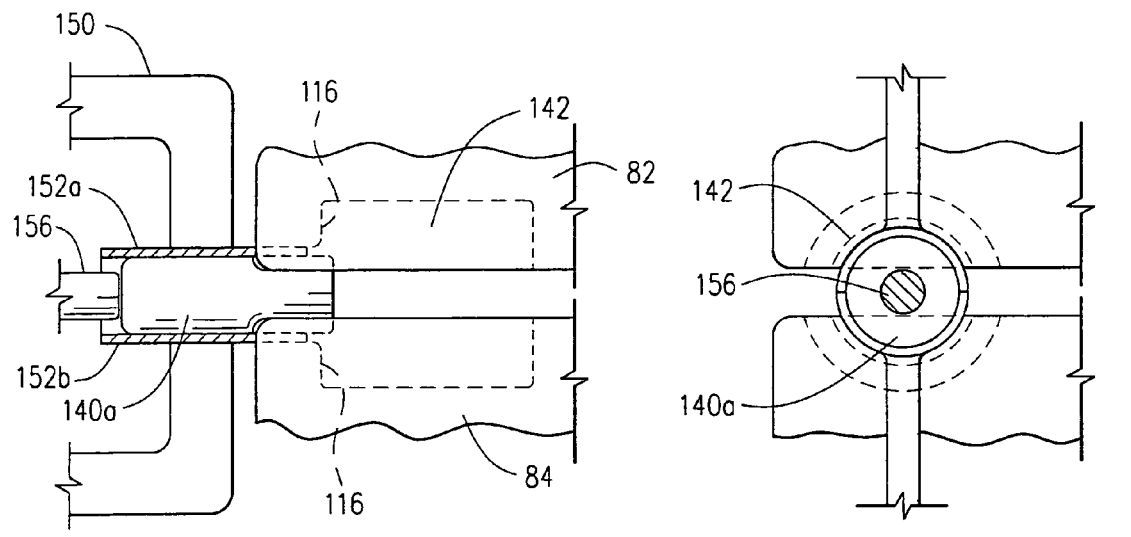
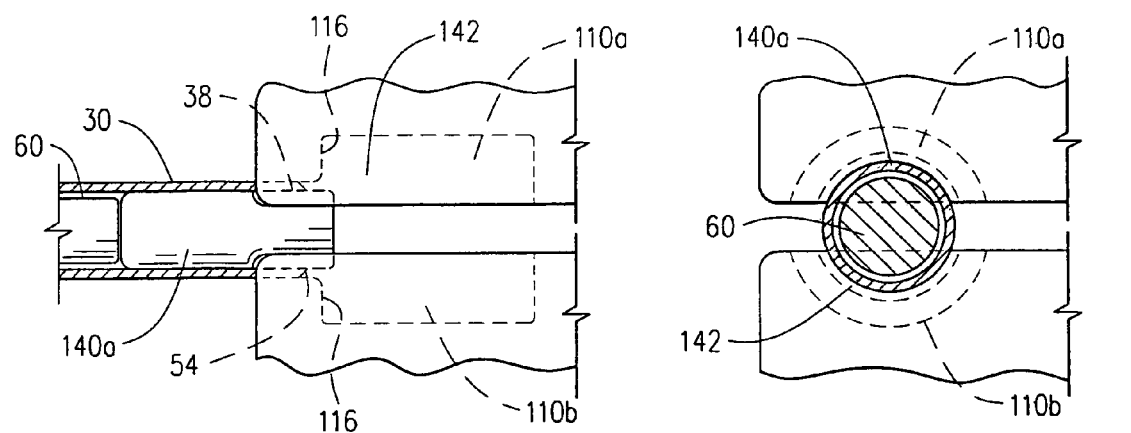

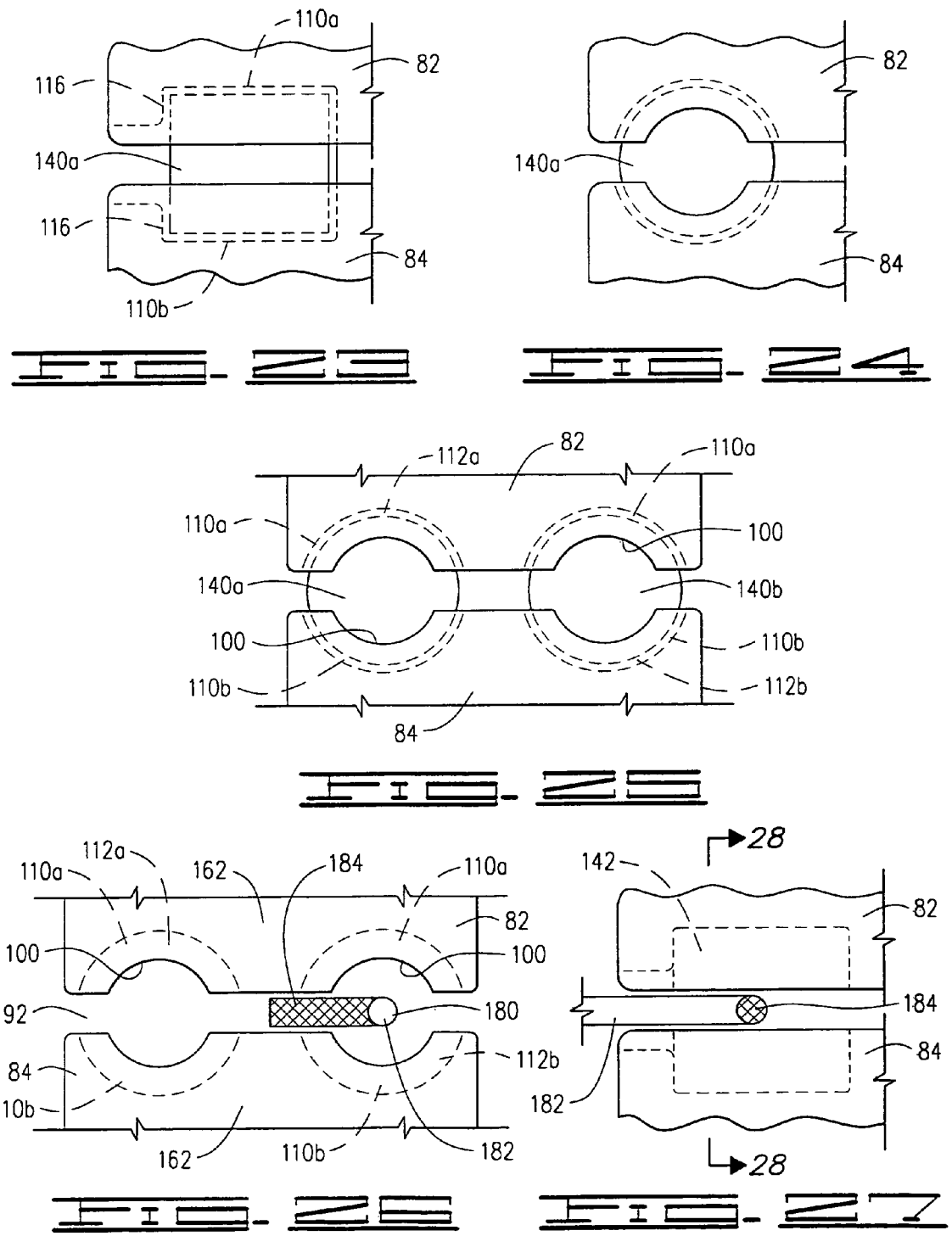

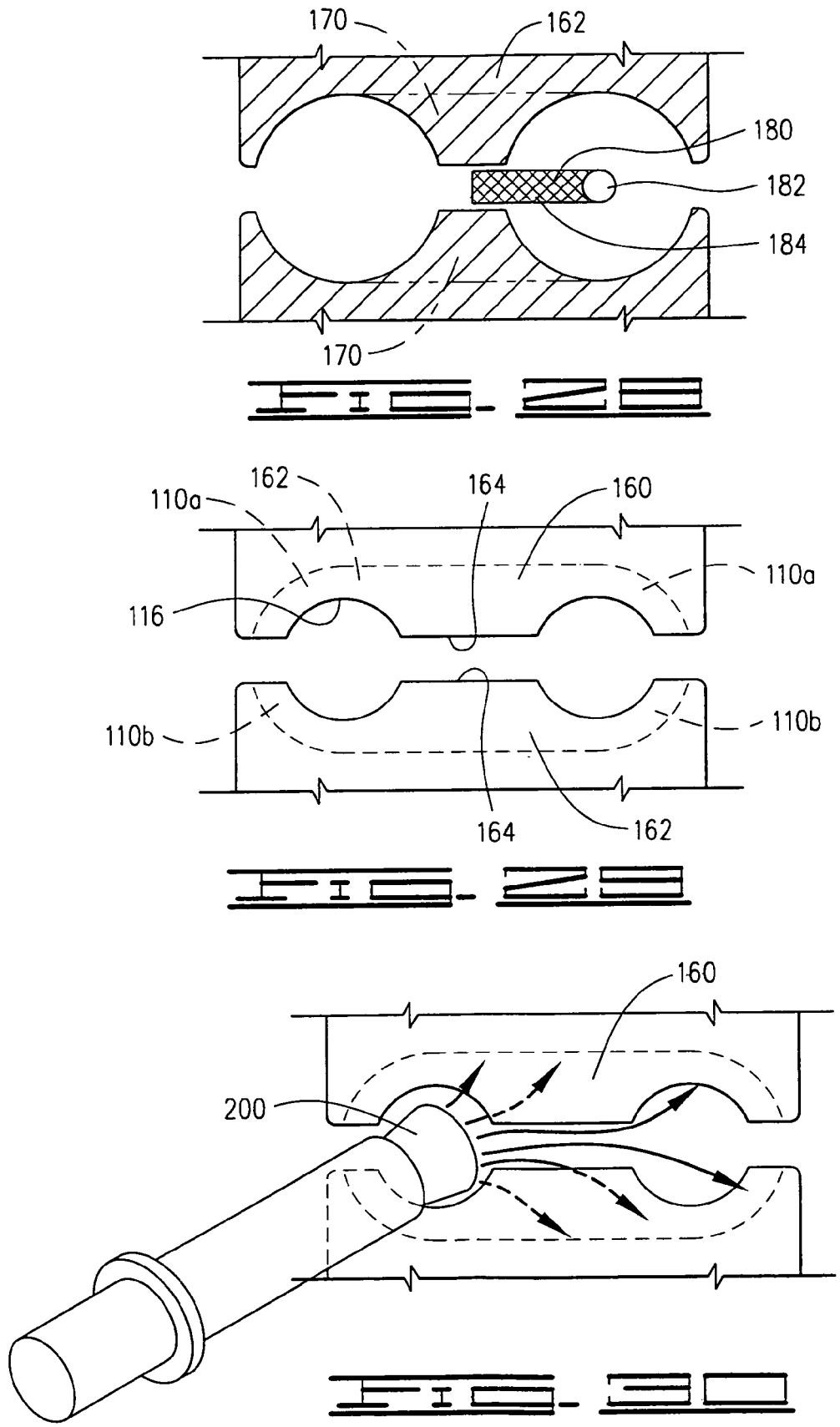

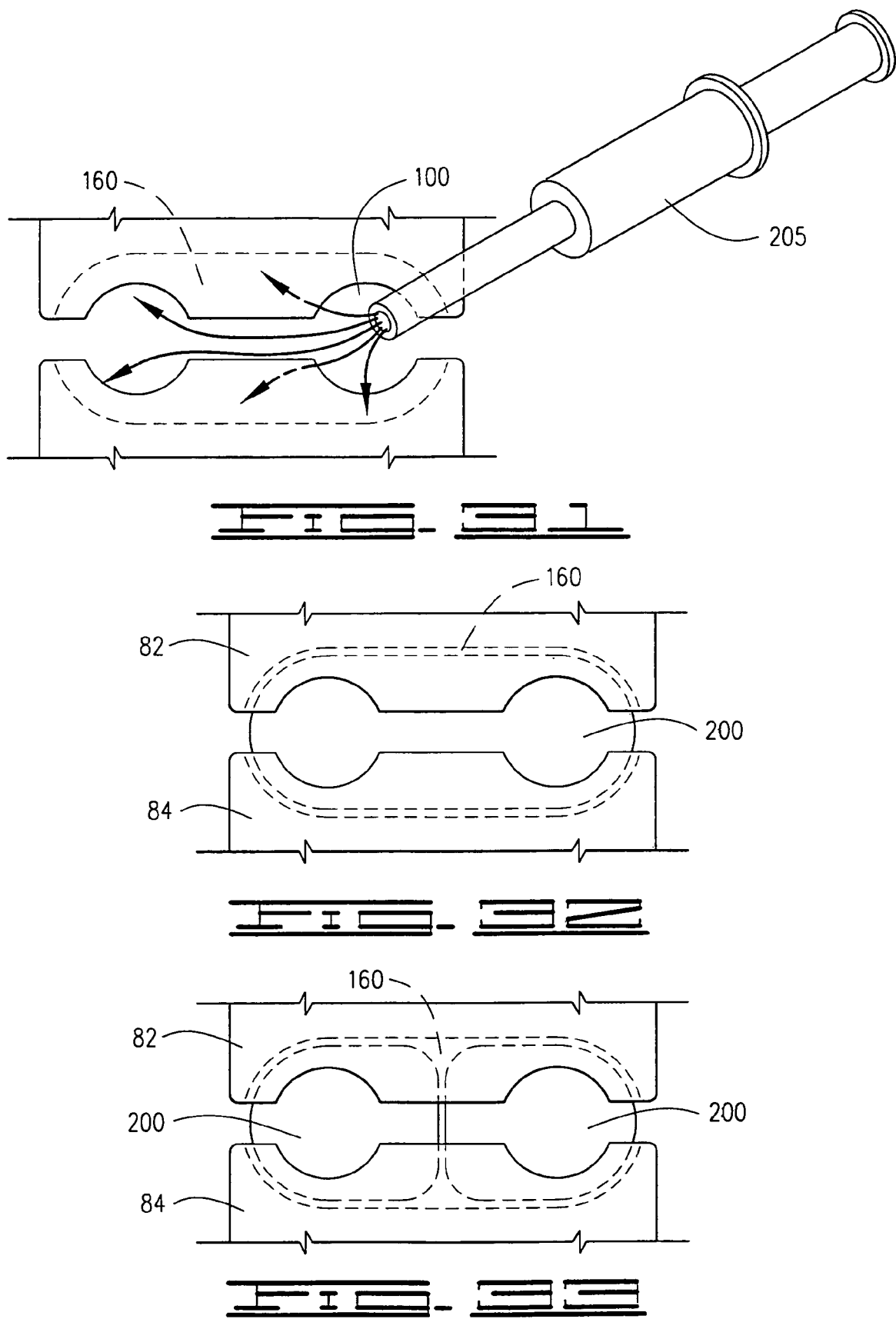

SPINAL DISC PROSTHESIS APPARATUS AND PLACEMENT METHOD

This Application is a Continuation-In-Part of application Ser. No. 10/995,886 filed on Nov. 23, 2004 which is a Continuation-In-Part of application Ser. No. 10/899,898 filed on Jul. 27, 2004.

BACKGROUND OF THE INVENTION

1. Field of the Invention

The present invention relates to spinal disc prostheses, methods of placing spinal disc prostheses between adjacent vertebrae and surgical instruments used in connection with the same.

2. Description of the Prior Art

The vertebrae of the human spine are each separated by a relatively soft disc which acts as a joint that allows the spine to flex, extend, bend laterally and rotate. Each disc includes a tough outer fibrous ring that binds the adjacent vertebrae together. The fibrous portion consists of overlapping multiple plies that are attached to the vertebrae in a manner that resists torsion whereby half of the angulated fibers making up the ring will tighten when the vertebrae rotate in either direction relative to each other. The inside of the disc has a high water content which aids in the load-bearing and cushioning properties of the disc.

Unfortunately, one or more discs in the spine can be displaced or damaged due to trauma or disease. A disc herniation occurs when the fibers are weakened or torn and the disc becomes permanently stressed, extended or extruded out of its normal confines. A herniated or slipped disc can compress a spinal nerve resulting in pain, loss of muscle control, or even paralysis. Also, the disc degeneration causes it to lose water and deflate. As a result, the height of the disc decreases causing it to buckle. As the buckling takes place, radial or annular tears may occur and contribute to persistent and disabling pain.

While a variety of disc prostheses and placement methods have been developed and used heretofore, they often involve fixed rigid approaches and systems which do not restore normal function and/or require long and complex operations. Flexible and relatively dynamic prostheses have been developed; however, many of such prostheses are too large to be inserted around the spinal nerves therefore cannot be placed using a posterior approach (through the back of the patient). Anterior approaches to disc replacement (through the abdomen of the patient) can be more difficult due to many factors, including possible injury to major blood vessels, a risk of impotence and other complications, and the inability to directly see pinched nerve elements. The assistance of a thoracic or vascular surgeon is often required when an anterior approach in utilized.

Thus, there is a need for a lumbar spinal disc prosthesis that can be easily placed between adjacent vertebrae using a posterior approach, that is relatively simple and that provides normal spine function without pain or disability. There is also a need for an improved method of placing a spinal disc prosthesis between adjacent vertebrae based on a posterior approach. Finally, there is a need for improved surgical instruments and apparatus for carrying out the placement procedure.

SUMMARY OF THE INVENTION

The present invention provides an improved spinal disc prosthesis, a spinal disc prosthesis insertion apparatus, a method of placing the prosthesis between adjacent vertebrae of a patient (e.g., a human patient) and surgical instruments for use in connection with the same. Although the inventive prosthesis, apparatus, method and instruments can be used in connection with any mammal, they are primarily designed and particularly suitable for use in replacing degenerated spinal discs of human beings.

The inventive spinal disc prosthesis can comprise one or more solid, compressible prosthesis elements that are formed prior to the method of placing the prosthesis. In one embodiment, the prosthesis consists of two, solid compressible prosthesis elements, each having a circular cross-section and the shape of a cylinder. In another embodiment, the prosthesis consists of a single, solid compressible prosthesis element having an oval cross-section. As described below, the solid compressible prosthesis elements are compressed prior to being inserted between adjacent vertebrae. The prosthesis elements can be compressed during the procedure, for example, at the operating table. The prosthesis elements can also be pre-compressed at the factory, for example, and used in association with the inventive spinal disc prosthesis insertion apparatus described below.

The inventive spinal disc prosthesis insertion apparatus comprises a shell and a compressed, solid compressible prosthesis element slidably disposed in the shell. The shell includes a hollow interior, an open upper end, and an open lower end opposing the open upper end. The prosthesis element can be pre-compressed and inserted into the shell at a time and location remote from the placement procedure; i.e., remote from the operating table. For example, the prosthesis element can be pre-compressed and inserted into the shell at the factory where the element is made. In carrying out the inventive method of placing the spinal disc prosthesis between adjacent spinal vertebrae, the open lower end of the shell is placed between adjacent vertebrae, and the prosthesis element is merely pushed from the shell into the proper position. The shell can then be disposed.

The inventive spinal disc prosthesis can also comprise one or more solid prosthesis elements that are formed in situ, that is, the material forming the prosthesis element(s) is placed in position between the adjacent vertebrae in a liquid or slurry form and then caused or allowed to harden in place.

The inventive method of placing a spinal disc prosthesis between adjacent vertebrae of a patient can be carried out using a posterior approach, that is, the prosthesis can be placed in position through the back of the patient. The method can be used to access the anterior column (anterior $\frac{2}{3}$ of the vertebral bodies). The solid, compressible prosthesis element or elements used in the method can each be compressed to a size that allows the element to be inserted into the interiors of adjacent spinal vertebrae between the adjacent vertebrae through the back of the patient. The need for retraction of spinal nerves and surrounding dura is minimal. Once in position within the interiors of the vertebrae, the prosthesis element expands back to its original shape and is thereby trapped therein.

In a first embodiment, the inventive method is a method of placing a spinal disc prosthesis including two solid prosthesis elements between adjacent spinal vertebrae. The method comprises the following steps:

First, an enlarged partially circular space is formed from the back and to one side of the space between adjacent vertebrae previously occupied by a degenerated disc. For example, a drill bit can be used to form the enlarged partially circular space. Additional spaces within the interiors of the adjacent vertebrae are then formed. Each of the additional spaces intersect the enlarged, partially circular space and include an upper surface adjacent to the enlarged, partially circular space. The additional spaces can be formed using a router specially constructed in accordance with the invention and described below.

Next, one of the two solid prosthesis elements is placed in the portion of the enlarged partially circular space that intersects the additional spaces and in the additional spaces whereby the upper surfaces of the additional spaces prevent the prosthesis element from coming out of the additional spaces. If the prosthesis to be inserted consists of two, solid compressible prosthesis elements, for example, one of the two elements is compressed and placed in the portion of the enlarged space that intersects the additional spaces and in the additional spaces within the interiors of the adjacent vertebrae. The compressible element can be compressed during the procedure using, for example, pliers apparatus or thumbscrew apparatus specially constructed in accordance with the invention. Alternatively, a compressible prosthesis element can be put into place using the inventive spinal disc prosthesis insertion apparatus described above. Either way, the compressed element is pushed into the additional spaces between the interiors of the adjacent vertebrae by way of the enlarged, partially circular space between the vertebrae wherein the compressed cylinder expands to its original shape. That is, the solid, compressed cylinder is placed in the portion of the enlarged, partially circular space that intersects the additional spaces and allowed to expand into the additional spaces. If the prosthesis element is to be formed in situ, the liquid or slurry material used to form the prosthesis element is injected or otherwise placed in the additional spaces between the adjacent vertebrae by way of the enlarged, partially circular space between the vertebrae. The material fills the additional spaces and the portion of the enlarged circular space intersecting the same. The material is then caused or allowed to harden. The upper surfaces of the additional spaces prevent the expanded solid, compressible prosthesis element or the hardened prosthesis element formed in situ from coming out of the additional spaces.

Thereafter, the same steps described above are repeated from the back and to the other side of the space between the adjacent vertebrae to place the second prosthesis element between the adjacent vertebrae. The additional spaces within the interiors of the adjacent vertebrae are vertically aligned. The two prosthesis elements are trapped and held firmly in place in the spaces within the interiors of the adjacent vertebrae by the upper surfaces of the additional spaces (which are a bony lip or edge of bone) and function together in the same manner as a normal vertebrae disc.

In a second embodiment, the inventive method is a method of placing a spinal disc prosthesis including one or more solid prosthesis elements between adjacent spinal vertebrae. This embodiment is similar to the first embodiment of the method described above in that an enlarged partially circular space and additional spaces that each intersect the enlarged partially circular space and include upper surfaces adjacent to the enlarged partially circular space are formed from the back and on each side of the space between adjacent vertebrae. Prior to inserting a prosthesis element, however, the interior spaces are interconnected to form an enlarged disc cavity within the interiors of the adjacent vertebrae. A single solid prosthesis element or two or more prosthesis elements can then be placed in the enlarged disc cavity. This embodiment is particularly useful when bone resorption is an issue. More specifically, the second embodiment of the method includes the following steps.

First, a first enlarged partially circular space is formed from the back and to one side of the space between adjacent vertebrae previously occupied by a degenerated disc. A first set of additional spaces is then formed within the interiors of the adjacent vertebrae, each of the additional spaces of the first set intersecting the first enlarged partially circular space and including an upper surface adjacent to the first enlarged partially circular space.

Next, a second enlarged partially circular space is formed from the back and to the other side of the space between the adjacent vertebrae previously occupied by the degenerated disc. A second set of additional spaces are then formed within the interiors of the adjacent vertebrae, each of the additional spaces of the second set intersecting the second enlarged partially circular space and including an upper surface adjacent to the second enlarged partially circular space. As with the first embodiment of the inventive method, a drill bit can be used to form the first and second enlarged partially circular spaces. The first and second sets of additional spaces can be formed within the interiors of the adjacent vertebrae using a router specially constructed in accordance with the invention and described below.

As a next step, the first set of additional spaces, the second set of additional spaces and the portions of the first and second enlarged partially circular spaces that intersect the respective additional spaces are interconnected to form an enlarged disc cavity within the interiors of the adjacent vertebrae. The enlarged disc cavity includes an upper surface between the first and second enlarged partially circular spaces and includes the upper surfaces of the first and second sets of additional spaces. The spaces are interconnected by removing the bone nubbins of the adjacent vertebrae remaining between the spaces. A rasp specially constructed in accordance with the invention, as described below, can be used to carry out this step.

Thereafter, a solid prosthesis element is placed in the enlarged disc cavity whereby the upper surfaces of the enlarged disc cavity prevent the prosthesis element from coming out of the first and second enlarged partially circular spaces. In one embodiment, a single, solid compressible prosthesis element of a size sufficient to essentially fill the enlarged disc cavity is utilized. In another embodiment, two solid compressible prosthesis elements that together are of a size sufficient to essentially fill the enlarged disc cavity are utilized. The compressible prosthesis element or elements can be compressed during the procedure using, for example, pliers apparatus or thumbscrew apparatus specially constructed in accordance with the invention. Alternatively, the compressible prosthesis element or elements can be put into place using the inventive spinal prosthesis insertion apparatus described above. For example, when a single compressible prosthesis element is utilized, the compressed element is pushed into the enlarged disc cavity by way of one of the enlarged partially circular spaces formed between the adjacent vertebrae. Once in the enlarged disc cavity, the compressed cylinder expands to fill the cavity.

As with the first embodiment of the inventive method, a single prosthesis element or two or more prosthesis elements can be formed in the enlarged disc cavity in situ. For example, the liquid or slurry material used to form the prosthesis element can be injected or otherwise placed in the enlarged disc cavity by way of one of the enlarged partially circular spaces between the vertebrae. Enough material (including the catalyst in a two-component system) is utilized to fill the entire enlarged disc cavity. The material is then caused or allowed to harden.

The upper surfaces of the enlarged disc cavity prevent the expanded solid, compressible prosthesis element(s) or the prosthesis element(s) formed in situ from coming out of the additional spaces. The prosthesis element(s) are trapped in the enlarged disc cavity and function in the same manner as a normal vertebra disc.

The present invention also includes a router for forming additional spaces within the interiors of adjacent spinal vertebrae that intersect an enlarged partially circular space formed from the back and to one side of a space between the adjacent vertebrae that was previously occupied by a degenerated disc. The router comprises an enlarged cylindrical portion of a size sufficient to form the additional spaces and having a diameter equal to or slightly less than the diameter of the enlarged partially circular space. The enlarged cylindrical portion includes a flat upper surface, a flat lower surface and a cylindrical body connecting the upper surface to the lower surface. The cylindrical body includes a plurality of sharp cutting points on the outside surface thereof for forming the additional spaces. A cylindrical shaft extends outwardly from the upper surface of the enlarged cylindrical portion. The shaft has a diameter substantially less than the diameter of the enlarged cylindrical portion.

The invention also includes a rasp that is particularly suitable for removing the bone nubbins between the spaces formed within the interiors of adjacent vertebrae to interconnect the spaces. The rasp comprises an elongated shaft and a file portion attached to the shaft and transversely extending therefrom. The file portion preferably extends substantially perpendicularly from the elongated shaft, more preferably at a 90 degree angle from the elongated shaft.

Various apparatus have been developed in accordance with the invention for compressing the solid, compressible elements to the necessary size and placing the compressed cylinders in the proper position between the vertebrae when solid, compressible elements are used in accordance with the inventive methods. For example, pliers apparatus or thumbscrew apparatus specially constructed in accordance with the invention can be used.

The objects, features and advantages of the present invention will be readily apparent to those skilled in the art upon a reading of the description of preferred embodiments which follows.

BRIEF DESCRIPTION OF THE DRAWINGS

FIG. 4 is a perspective view of the inventive spinal disc prosthesis insertion apparatus having a single compressed prosthesis element loaded therein.

FIG. 5 is a perspective view of the inventive spinal disc prosthesis insertion apparatus having two compressed prosthesis elements loaded therein.

FIG. 6 is a side sectional view showing the upper end of the spinal disc prosthesis insertion apparatus illustrated by FIGS. 4 and 5.

FIG. 7 is a side sectional view showing the lower end of the spinal disc prosthesis insertion apparatus illustrated by FIGS. 4, 5 and 6.

FIG. 8 is a perspective view of a plunger for use in pushing the prosthesis element(s) out of the spinal disc prosthesis insertion apparatus illustrated by FIGS. 4-7.

FIG. 9 is an elevation view of a drill bit for use in forming an enlarged partially circular space between adjacent spinal vertebrae in accordance with the invention.

FIG. 10 is an elevation view of the inventive router.

FIG. 11 is a cross-sectional view taken along lines 11-11 of FIG. 10.

FIG. 12 is an elevation view of the inventive rasp.

FIG. 13 is a top view of the rasp illustrated by FIG. 12.

FIG. 14 is a back view of the spine showing adjacent vertebrae having a degenerated disc therebetween.

FIG. 14A is a back view of the spine showing the adjacent vertebrae with the degenerated disc removed and a disc distractor and collar in place.

FIG. 19 is a partial side view of the adjacent vertebrae illustrating a compressed solid compressible prosthesis element being pushed with a rod through the clamped together opposing cylindrical jaws of the pliers apparatus illustrated by FIGS. 34 and 35 and into position within interiors of the adjacent vertebrae.

FIG. 20 is a partial back view of the adjacent vertebrae illustrating the compressed solid compressible prosthesis element being pushed with the rod shown by FIG. 19 into position within interiors of the adjacent vertebrae.

FIG. 21 is a partial side view of the adjacent vertebrae illustrating a compressed solid compressible prosthesis element being pushed with the plunger illustrated by FIG. 8 through the spinal disc prosthesis insertion apparatus illustrated by FIGS. 4-7 and into position within interiors of the adjacent vertebrae.

FIG. 22 is a partial back view of the adjacent vertebrae showing the compressed solid compressible prosthesis element being pushed with the plunger into position within the interiors of the adjacent vertebrae.

FIG. 23 is a partial side view of the adjacent vertebrae after the solid compressible prosthesis element (a cylinder in this case) has been placed and allowed to expand in the spaces within the interiors of the adjacent vertebrae.

FIG. 24 is a back view of the adjacent vertebrae after the solid compressible prosthesis element (a cylinder in this case) has been placed and allowed to expand in the spaces within the interiors of the adjacent vertebrae.

FIG. 25 is a back view of the spine showing two solid compressible prosthesis elements (cylinders in this case) placed between adjacent vertebrae in accordance with the invention.

FIG. 26 is a back view of the spine illustrating insertion of the rasp illustrated by FIGS. 12 and 13 to remove the bone nubbins between the spaces formed within the interiors of adjacent vertebrae to interconnect the spaces and form a single, enlarged disc cavity within the interiors of adjacent vertebrae.

FIG. 27 is a partial side view of the adjacent vertebrae further illustrating insertion of the rasp to remove the bone nubbins.

FIG. 28 is a cross-sectional view taken along lines 28-28 of FIG. 27.

FIG. 29 is a back view of the spine showing the single, enlarged disc cavity formed within the interiors of adjacent vertebrae by removing the bone nubbins between the formed spaces and interconnecting the spaces.

FIG. 30 is a back view of the spine illustrating the disc prosthesis illustrated by FIG. 2 being inserted into the enlarged disc cavity using the spinal disc prosthesis insertion apparatus illustrated by FIGS. 4-7.

FIG. 31 is a back view of the spine illustrating injection of a liquid or slurry form of the inventive spinal disc prosthesis into the enlarged disc cavity.

FIG. 32 is a back view of the spine illustrating the compressible disc prosthesis illustrated by FIG. 2 after the prosthesis has been inserted into the enlarged disc cavity formed within the interiors of adjacent vertebrae. FIG. 28 also illustrates the disc prosthesis formed by injecting a liquid or slurry material into the enlarged disc cavity as shown by FIG. 31 and causing or allowing the material to harden in accordance with the invention.

FIG. 33 is a back view of the spine illustrating the compressible disc prosthesis illustrated by FIG. 3 after the prosthesis has been inserted into the enlarged disc cavity formed within the interiors of adjacent vertebrae.

DESCRIPTION OF PREFERRED EMBODIMENTS

Figure 1:
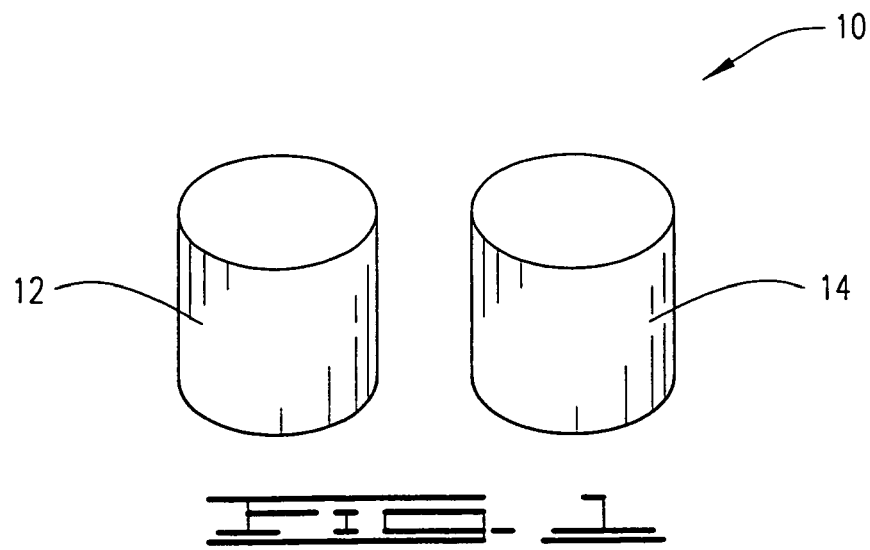
FIG. 1 is a perspective view of one embodiment of the inventive spinal disc prosthesis.

In accordance with the present invention, an improved intervertebral, lumbar disc prosthesis, a spinal disc prosthesis insertion apparatus, a method of placing the prosthesis between adjacent vertebrae of a human patient and surgical instruments for use in connection with the same are provided. The inventive prosthesis is used to replace the natural disc that separates and cushions adjacent spinal vertebrae when the natural disc has degenerated. The loss of the natural disc causes the adjacent vertebrae to lose physiological motion and stability.

A variety of surgical procedures have been utilized to address the problem when a disc degenerates. These procedures have included replacement of the degenerated spinal disc with a spinal disc prosthesis. They have also included fusing or otherwise directly connecting the adjacent vertebrae together. Generally, the surgical procedures used heretofore have been only partially successful. In many cases, normal physiological functions (e.g., motion and load-cushioning in all directions of force) are not restored. Furthermore, due to their size, many of the disc prostheses utilized heretofore can only be placed in position by an anterior approach, that is, through the abdomen of the patient. Inserting the prosthesis through the abdomen of the patient typically requires the assistance of a thoracic surgeon to move organs, etc. and is much more involved than a procedure based on a posterior approach. Unfortunately, due to spinal nerves and surrounding dura, there is a very small amount of room available for the prosthesis to be placed from the posterior making the size of the prosthesis element a limiting factor when a posterior approach is used. Retraction of the spinal nerves should be minimal; the nerves certainly cannot be retracted across the sagittal midline, for example. Also, it can be difficult to see nerve roots and the like when using anterior, anterior-lateral and posterior-lateral approaches.

The inventive method of placing a spinal disc prosthesis between adjacent vertebrae of a patient is based on a posterior approach, that is, the prosthesis is placed in position through the back of the patient. For example, the solid, compressible prosthesis elements of the invention can each be compressed to a size that allows the element to be inserted into the interiors of the adjacent spinal vertebrae between the adjacent vertebrae (the vertebra above and the vertebra below, spanning the disc space) through the back of the patient. The need for retraction of the spinal nerves and surrounding dura is minimal. The procedure involves direct exposure of nerve roots and the like which allows ruptured disc fragments and bone spurs to be removed as necessary to unpinch pinched nerves.

The inventive method for placing the prosthesis between adjacent spinal vertebrae greatly reduces costs as compared to rigid fixation and other surgical techniques heretofore utilized, and provides a relatively simple and easily accomplished surgical procedure. The inventive method and disc prosthesis provide normal motion, cushioning and stabilization for a long period of time. There are no prolonged side effects from the procedure. Further, after a period of time, if degeneration of the inventive spinal disc prosthesis occurs, the disc prosthesis can be easily and quickly replaced using microendoscopic paramedian approach technologies. Like the procedure for initially placing the spinal disc prosthesis between adjacent spinal vertebrae, the procedure for replacing the inventive disc prosthesis involves direct exposure of nerve roots and the like as desired and the entire procedure may be accomplished by means of a back approach only.

Figure 2:
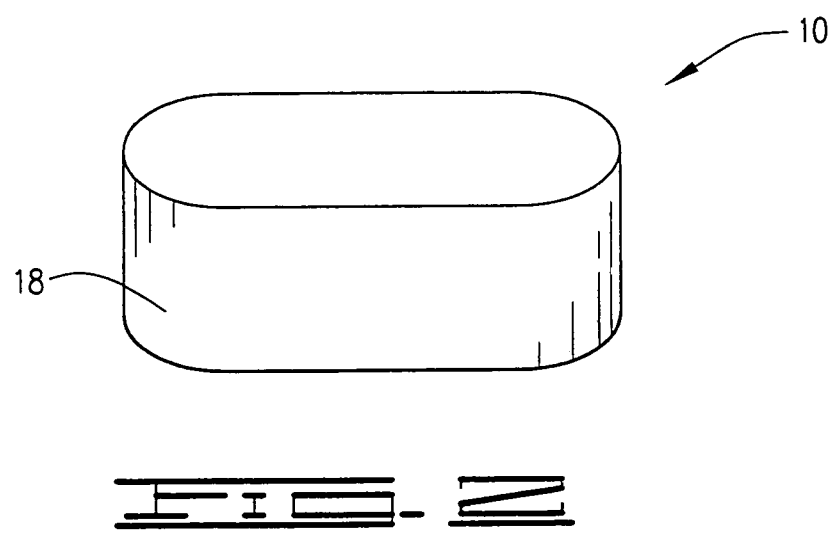
FIG. 2 is a perspective view of another embodiment of the inventive spinal disc prosthesis.
Figure 3:
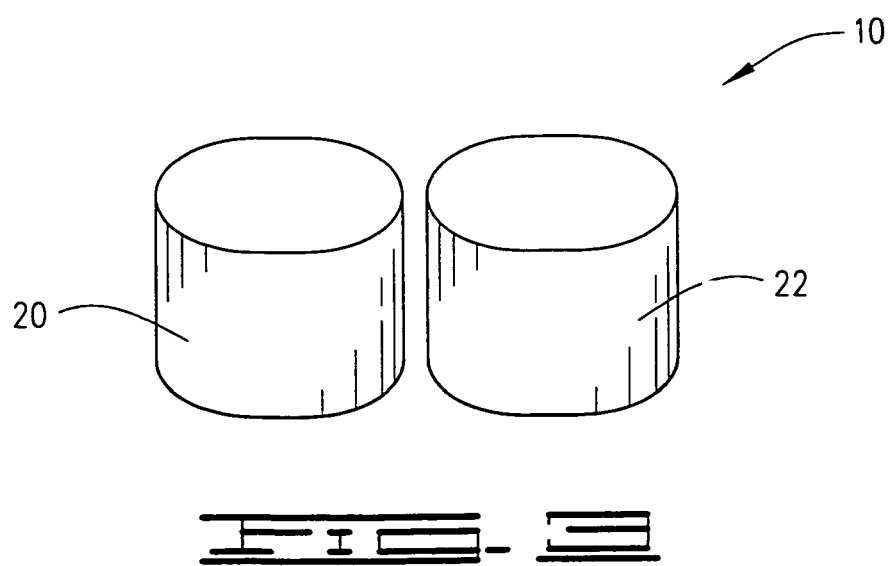
FIG. 3 is a perspective view of yet another embodiment of the inventive spinal disc prosthesis.

Referring now to FIGS. 1-3 of the drawings, the inventive spinal disc prosthesis can comprise one or more solid, compressible prosthesis elements that are formed prior to the method of placing the prosthesis between adjacent spinal vertebrae. Each compressible prosthesis element can be compressed to a size that allows the element to be inserted between the adjacent vertebrae (the vertebra above and the vertebra below, spanning the disc space) through the back of the patient. This important feature distinguishes the inventive spinal disc prosthesis from other prostheses or prostheses elements that are too large to be inserted using a posterior approach. Once within the interiors of the adjacent vertebrae, the compressed prosthesis element expands back to its original shape (or at least close thereto) which results in the prosthesis element being trapped within the interiors of the adjacent vertebrae which is another important feature of the invention.

Each prosthesis element of the inventive disc prosthesis is formed of a solid, rubbery compressible material which deforms at pressures in the range of from about 5 psi to about 600 psi, preferably from about 400 psi to about 600 psi, and expands back to its original shape (or close thereto) after it is compressed. When the disc prosthesis includes more than one prosthesis element, the elements are preferably identical in size, shape and composition.

A variety of plastics, polymers (including elastomers) and other compressible rubbery materials that expand back to their original shape (or essentially their original shape) after they are compressed can be used to form the prosthesis element or elements of the inventive spinal disc prosthesis. The material utilized should be durable, have good abrasion breakdown characteristics and be biocompatible with respect to the human body. It needs to be stiff enough to resist abrasion (e.g., firm like a hockey puck), yet capable of being compressed to a size small enough to be inserted in accordance with the inventive method. Suitable materials include, but are not limited to, polyurethane, polyurethane coated with a material that makes the element inert with respect to the patient's body, polypropylene, polyethylene, polytetrafluoroethylene and polydimethylsiloxane. An example of a material that can make the prosthesis element inert with respect to the patient's body is "SILASTIC™," a rubbery coating having physical characteristics comparable to rubber before rubber is vulcanized, but containing organosilicone polymers and having excellent resistance to compression set. "SILASTIC™" is commercially available from Dow Corning Corp. of Midland, Mich. The prosthesis element or elements of the inventive disc prosthesis can also be made entirely of "SILASTIC™." Preferably, the material used to form the prosthesis element or elements of the inventive spinal disc prosthesis is a high density, abrasion resistant and biocompatible polyurethane or polyethylene, most preferably polyethylene.

FIG. 1 illustrates an embodiment of the inventive spinal disc prosthesis that is particularly suitable for use in connection with the first embodiment of the inventive method, that is, the embodiment of the inventive method wherein the interior spaces between the adjacent vertebrae are not interconnected. As shown by FIG. 1, this embodiment of the inventive spinal disc prosthesis, generally designated by the reference numeral 10, consists of two solid, compressible prosthesis elements 12 and 14, each having a circular cross-section and a cylindrical shape. As described in connection with the first embodiment of the inventive method described below, one of the cylinders is placed on one side of the space between the adjacent vertebrae, and the other cylinder is placed on the other side of the space between the adjacent vertebrae.

FIG. 2 illustrates an embodiment of the inventive spinal disc prosthesis 10 that is particularly suitable for use in connection with the second embodiment of the inventive method, that is, the embodiment of the inventive method wherein the interior spaces between adjacent spinal vertebrae are interconnected to form an enlarged disc cavity. In this embodiment, the spinal disc prosthesis 10 is a single, compressible prosthesis element 18. Again, as with all of the prosthesis elements of the inventive spinal disc prosthesis 10, the embodiment shown by FIG. 2 can be compressed to a size that allows the element to be inserted through the back of the patient into the enlarged disc cavity formed within the interiors of adjacent spinal vertebrae of the patient. As shown, this embodiment has an oval cross-section.

FIG. 3 illustrates another embodiment of the inventive spinal disc prosthesis 10 that can be used in association with the second embodiment of the inventive method, that is, the embodiment of the inventive method wherein the spaces within the interiors of the adjacent spinal vertebrae are interconnected to form a single, enlarged disc cavity therein. In this embodiment, the inventive spinal disc prosthesis 10 consists of two solid compressible prosthesis elements 20 and 22, each having an oval cross-section. The prosthesis elements 20 and 22 are placed side by side in the enlarged disc cavity and together form a prosthesis element that is about the same size as the prosthesis element 18 shown by FIG. 2.

The embodiments of the inventive spinal disc prosthesis shown by FIGS. 1-3 can be compressed during the procedure, for example, at the operating table, using compression apparatus constructed in accordance with the invention as described below. The prosthesis elements shown by FIGS. 1-3 can also be pre-compressed at the factory, for example, and used in association with the inventive spinal disc prosthesis insertion apparatus described below.

The inventive spinal disc insertion apparatus is shown by FIGS. 4-7 and generally designated by the reference numeral 30. The spinal disc prosthesis insertion apparatus 30 comprises a shell 32 including a hollow interior 34, an open upper end 36, and an open lower end 38 opposing the open upper end. One, two or more compressed, solid compressible prosthesis elements 40 (shown by the dotted lines in FIGS. 4 and 5) are slidably disposed in the shell 32. The prosthesis element or elements 40 can be any one of the prosthesis elements 12, 14, 18, 20 or 22 in their compressed form. As shown, the shell 32 is an elongated tube having a circular cross-section. Thus, when one of the prosthesis elements 12 and 14 is used, for example, the shell 32 and the prosthesis element each have a circular cross-section.

The spinal disc insertion apparatus 30 further includes a finger tab 44 disposed adjacent to the upper end 36 of the shell 32. The finger tab 44 radially extends outwardly from the perimeter of the shell 32, preferably perpendicularly with respect to the longitudinal axis of the shell. The finger tab 44 has a diameter that is sufficiently larger than the diameter of the shell 32 to allow the shell to be grasped and held by the fingers of the user as the prosthesis element or elements 40 are pushed with a separate apparatus through the open lower end 34 of the shell. Preferably, the shell 32 and finger tab 44 are integrally formed of the same material.

A portion 50 of the outside surface 52 of the shell 32 adjacent to the lower end 38 of the shell is tapered to impart a coring surface 54 to the lower end of the shell. The coring surface 54 is sharp enough to facilitate insertion of the lower end 38 of the shell 32 into the enlarged partially circular space formed between the adjacent vertebrae, as described below.

The shell 32, including the finger tab 44, of the spinal disc prosthesis insertion apparatus can be formed of a variety of materials including, but not limited to, aluminum, copper, stainless steel or other metals and rigid plastics. Preferably, the shell 32, including the finger tab 44, is formed of a high density polymer or plastic. The shell 32 is preferably 125 to 150 mm long, has a 14 mm inside diameter and a 15 mm outside diameter. The inside surface of the shell 32 can be coated with "TEFLON" or a similar material in order to facilitate movement of the prosthesis elements therein. Also, the shell and/or prosthesis element(s) can be coated with a sterile lubricant, such as sterile mineral oil, to facilitate expulsion of the prosthesis element(s) from the shell.

The prosthesis element or elements 40 are preferably pre-compressed and inserted into the shell 32 of the spinal disc prosthesis insertion apparatus 30 at a time and location remote from the placement procedure; i.e., remote from the operating table. For example, the prosthesis element(s) 40 can be pre-compressed and inserted into the shell 32 at the factory where the element(s) are made. This facilitates the placement procedure, allows the procedure to be carried out in less time, assures the uniformity of the prosthesis element(s) and lowers the cost of the reusable instrument set to be used in connection with the procedure. A number of methods can be utilized to compress the prosthesis element(s) 40 and place them in the shell 32. For example, a flexible steel banding tape which encircles the fully-expanded prosthesis element can be used to circumferentially compress the prosthesis element to the desired size (by applying appropriate torque and pressure) for insertion into the shell 32. The prosthesis element can merely be pushed from the banding tape into the shell. As shown by FIGS. 4-7, the prosthesis element(s) 40 are preferably positioned into the shell 32 close to the lower end 38 of the shell in order to make it easier to push the element(s) out of the shell into position between the adjacent vertebrae. The entire apparatus 30, including the shell 32 and prosthesis element(s) 40, is preferably formed and packaged in a sterile manner so that it will be ready for use during the placement procedure.

FIG. 8 illustrates a plunger 60 that can be utilized during the placement procedure to push the prosthesis element(s) 40 out of the shell 32 of the spinal disc prosthesis insertion apparatus 30 into the appropriate space between the adjacent vertebrae. The plunger 60 is a solid member having a circular cross-section and has a diameter that is slightly less than the diameter of the shell 32. The plunger 60 includes an upper end 62, a lower end 64 and an elongated portion 66 connecting the upper end to the lower end. A finger tab 68 is disposed adjacent to the upper end 62 and radially extends outwardly from the perimeter of the elongated portion 66. The finger tab 68 and elongated portion 66 are preferably integrally formed out of stainless steel. The elongated portion 66 is approximately 125 to 150 mm long and has a 13 mm inside diameter. The edge 70 between the elongated portion 66 and the lower end 64 is slightly rounded to impart a smooth surface to the lower end. The plunger 60 can be included in the reusable instrument set for the procedure.

The inventive spinal disc prosthesis 10 can also comprise one or more solid prosthesis elements that are formed in situ, that is, the material forming the prosthesis element(s) is placed in position between the adjacent vertebrae in a liquid or slurry form and then caused or allowed to harden in place to a predetermined, desired firmness. A two-component system is preferably employed. For example, a base liquid or slurry can be added to the interior spaces between the vertebrae. A liquid catalyst can then be added (admixed with the base liquid or slurry) to cause the material to harden. The base liquid or slurry and catalyst fill the interior spaces (the bony cavities) and then harden to the desired final stiffness and density. Methyl methacrylate, commonly used as a bone substitute and in other spine work, is an example of a suitable material that is hardened by adding a catalyst thereto. Many polyurethane and polyethylene liquid or slurry materials that harden in place to a desired and predetermined firmness upon the addition of a liquid catalyst thereto are also commercially available and suitable for use in connection with the invention. Forming the prosthesis 10 in situ accomplishes the requirements of small exposure and safe placement and allows prosthesis elements of multiple sizes to be formed.

Prior to placing the inventive spinal disc prosthesis 10 between adjacent spinal vertebrae, a number of preliminary steps are carried out. First, the degenerated disc between the adjacent vertebrae, or a portion thereof, is removed. FIG. 14 is a back view of the spine 80 showing adjacent vertebrae 82 and 84 and a degenerated disc 86 between the vertebrae. If the first embodiment of the inventive method as described below is to be carried out, that is, if the spaces formed within the interiors of the adjacent vertebrae 82 and 84 are not to be interconnected, only the portions 86a and 86b of the degenerated disc 86 need to be removed. If the second embodiment of the inventive method is to be carried out, that is, if the spaces formed within the interior of the adjacent vertebrae 82 and 84 are to be interconnected to form an enlarged disc cavity within the interiors of the adjacent vertebrae, the portion 86c of the degenerated disc 86 also needs to be removed. The portion 86c of the degenerated disc 86 can be removed either as a preliminary step to the overall placement procedure or just prior to the time that the interior spaces are interconnected as shown below. If it is known ahead of time that the second embodiment of the inventive method will be carried out, the portions 86a, 86b and 86c of the degenerated disc 86 are preferably preliminarily removed at the same time. The degenerated disc 86 or portions thereof are preferably removed using a bilateral microscopic lumbar hemilaminotomy foramenotomy dissectomy, a standard procedure.

As shown by FIG. 14A, once the degenerated disc 86 or appropriate portions 86a, 86b and 86c thereof are removed, a disc distractor 90, a well-known instrument, is inserted in the space 92 between the vertebrae and utilized to move the vertebra 82 and vertebra 84 apart. The distractor 90 is placed between the adjacent vertebrae on the side opposite to that on which the initial work is to be performed. The distractor 90 is inserted between the vertebrae 82 and 84 and turned 90 degrees to push the vertebrae apart. The vertebrae are then lined up using x-ray equipment, and a steel collar 96 is placed in the proper position between the adjacent vertebrae. The collar 96 includes triangular tabs (not shown) that stick into the bone to hold the collar in place. The collar 96 serves as a drill guide and protective device.

Once the above preliminary steps have been completed, the inventive method is carried out. Referring now to FIGS. 15 through 25, a first embodiment of the inventive method will be described. In this embodiment, the method is used to place a spinal disc prosthesis including two solid prosthesis elements between the adjacent spinal vertebrae 82 and 84. The method includes the following steps.

Figures 15, 16:
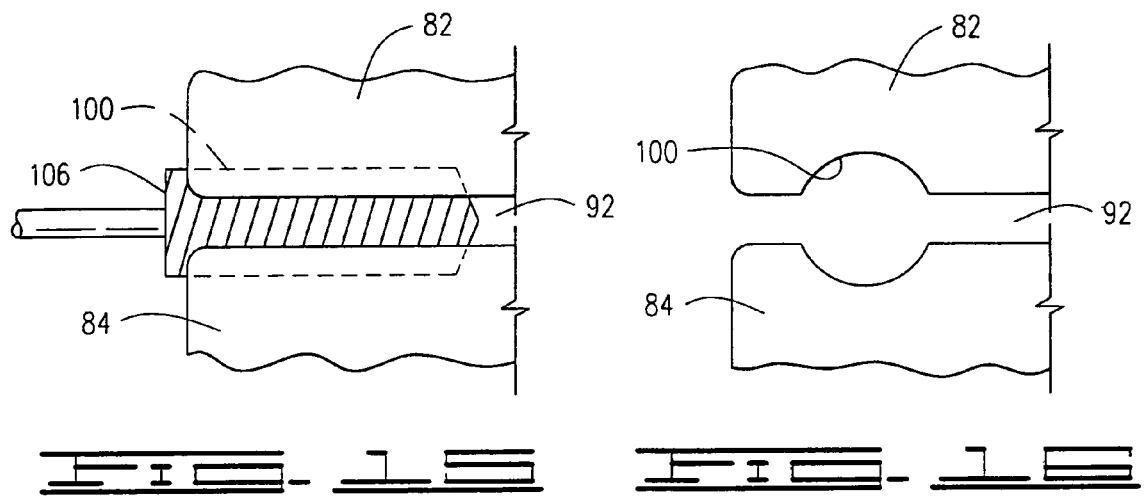
FIG. 15 a partial side view of adjacent vertebrae illustrating the enlarged partially circular space formed using the drill bit.
FIG. 16 is a partial back view of the adjacent vertebrae after the enlarged partially circular space between the adjacent spinal vertebrae has been formed.

First, as shown best by FIGS. 15 and 16, an enlarged partially circular space 100 is formed between the adjacent vertebrae 82 and 84 separated by the space 92 previously occupied by the degenerated disc 86. With the space 92 held apart by the distractor 90, the enlarged partially circular space 100 is formed from the back of the vertebrae 82 and 84 in the space 92 between the adjacent vertebrae. The drill bit 106 shown by FIG. 9 can be utilized to form the enlarged partially circular space 100. The drill bit 106 is a standard drill bit, preferably of a size of 9/16 of an inch in diameter. The collar 96 is preferably positioned on the adjacent vertebrae, as shown by FIG. 14A, and functions as a drill guide.

As shown by FIG. 15, using the drill bit 106, the enlarged partially circular space 100 is formed through the space 92 from the back to near the front of the adjacent vertebrae 82 and 84 on one side thereof. The space 100 preferably extends into to the adjacent vertebrae 82 and 44 for a distance that is at least about 2/3 of the width of the vertebrae (i.e., the length of the space 100 is at least about 2/3 of the width of the vertebrae). FIG. 16 is a partial back view of the adjacent vertebrae 82 and 84 showing the enlarged partially circular space 100 after it has been formed between the vertebrae.

Figures 17, 18:
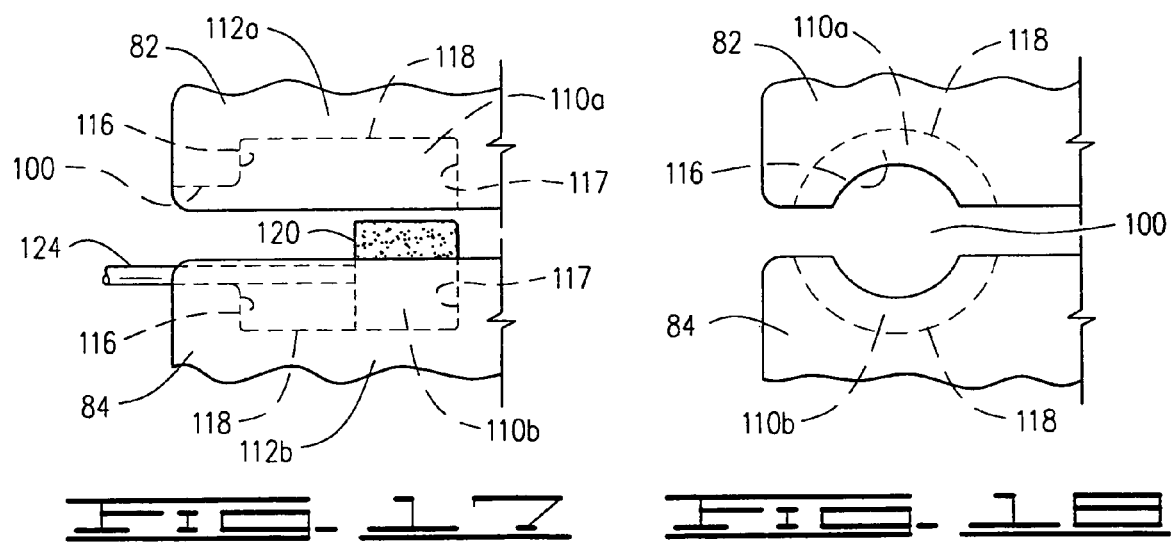
FIG. 17 is a partial side view of adjacent vertebrae showing the additional spaces formed by the router within the interiors of the adjacent vertebrae that intersect the enlarged space between the vertebrae.
FIG. 18 is a partial back view of the adjacent vertebrae after the enlarged partially circular space between the adjacent spinal vertebrae and the additional spaces within the interiors of the adjacent vertebrae have been formed.

Next, as illustrated by FIGS. 17 and 18, additional spaces 110a and 110b are formed within the interiors 112a and 112b of the adjacent vertebrae 82 and 84. Each of the additional spaces 110a and 110b intersects the enlarged partially circular space 100 and includes an upper surface 116 adjacent to the enlarged partially circular space 100. The additional spaces 110a and 110b also each include a lower surface 117 and a side wall 118.

The additional spaces 110a and 110b are preferably formed using a router 120. The router 120 is best shown by FIGS. 10 and 11. The router 120 comprises an enlarged cylindrical portion 122 and a cylindrical shaft 124. The enlarged cylindrical portion 122 is of a size sufficient to form the additional spaces 110a and 110b and has a diameter equal to or slightly less than the diameter of the enlarged partially circular space 100. Thus, the enlarged cylindrical portion 122 has a diameter equal to or slightly less than 9/16 of an inch. It is believed that 9/16 of an inch represents about the maximum diameter for the enlarged cylindrical portion in view of safety concerns (e.g., for proper placement between the common dura of spinal cord and dura of the nerve root sleeves). The enlarged cylindrical portion 122 includes a flat upper surface 126, a flat lower surface 128 and a cylindrical body 130 connecting the upper surface to the lower surface. The cylindrical body 130 is stippled; i.e., it includes a plurality of sharp cutting points 132 on the outside surface 134 thereof for forming the additional spaces 110a and 110b. The cutting points 132 cover the entire outside surface 134 of the cylindrical body 132 and are sharp enough to cut bone as needed but smooth and fine-textured enough to act, in effect, as sandpaper to impart a surface of bone upon rotation of the router that is much smoother than it would be if a spiral fluted drill bit was used, for example.

The fact that the upper surface 126 of the enlarged cylindrical portion 122 is smooth and flat is very important in that it imparts smooth and flat surfaces to the upper surfaces 116 of the additional spaces 110a and 110b. Similarly, the fact that the lower surface 128 of the enlarged cylindrical portion 122 is smooth and flat is important in that it imparts a smooth and flat surface to the lower surfaces 117 of the additional spaces 110a and 110b. Finally, the fact that the cylindrical body 130 of the enlarged cylindrical portion 122 is stippled (i.e., includes a plurality of sharp cutting points), as opposed to fluted, for example, is important in that it imparts smooth surfaces to the side walls 118 of the additional spaces 110a and 110b. If the surfaces of the additional spaces 110a and 110b are rough or jagged, the durability and function of the inventive spinal disc prosthesis 10 would be adversely affected. Rough or jagged surfaces can cause significant abrasion to the prosthesis element(s) over time. Furthermore, the vertebrae material surrounding the additional spaces 110a and 110b might be punctured or otherwise adversely impacted if the upper and lower surfaces 126 and 128 of the enlarged cylindrical portion 122 were not flat or if a different type of cutting means was included on the outside surface of the cylindrical portion 122.

The cylindrical shaft 124 of the router 120 extends outwardly from the upper surface 126 of the enlarged cylindrical portion 132. The shaft 124 has a diameter substantially less than the diameter of the enlarged cylindrical portion 122. Preferably, the diameter of the shaft is approximately ⅛ of an inch. A diameter of ⅛ of an inch is large enough to impart the necessary structural integrity to the router yet small enough to allow the additional spaces to be formed. The relatively small ratio of the diameter of the shaft 124 to the diameter of the enlarged cylindrical portion 122 allows the additional spaces 110a and 110b to be of a size sufficient for the inventive spinal disc prosthesis. The shaft 124 preferably has a length of about four (4) inches. A shaft having a diameter of ⅛ of an inch and a length of 4 inches allows the enlarged cylindrical portion 122 to "wobble" which helps smooth off the surface of the drilled vertebrae thereby reducing abrasion to the prosthesis.

As shown by FIG. 17, the enlarged cylindrical portion 122 of the router 120 is inserted in the enlarged partially circular space 100 formed between the vertebrae 82 and 84 by the drill bit 106. The router 120 is then moved up and down within the interiors 112a and 112b of the adjacent vertebrae 92 and 94 whereby the additional spaces 110a and 110b are formed in the adjacent vertebrae. FIG. 18 is a partial back view of the adjacent vertebrae 82 and 84 after the enlarged partially circular space 100 and the additional spaces 110a and 110b have been formed. Again, because the shaft 124 of the router 120 has a relatively small diameter when compared to the diameter of the enlarged cylindrical portion 122 of the router, the enlarged cylindrical portion 122 of the router can extend into the adjacent vertebrae 82 and 84 the distances required to form the additional spaces 110a and 110b. FIG. 18 is a partial back view of the adjacent vertebrae 82 and 84 showing the additional spaces 110a and 110b after they have been formed between the vertebrae 82 and 84.

Referring now to FIGS. 19-24, after the additional spaces 110a and 110b are formed within the interiors 112a and 112b of the adjacent vertebrae 82 and 84, one of the two solid prosthesis elements, prosthesis element 140a, is placed in the portion 142 of the enlarged partially circular space 100 that intersects the additional spaces and in the additional spaces. The upper surfaces 116 of the additional spaces 110a and 110b prevent the prosthesis element 140a from coming out of the additional spaces. If the prosthesis 10 to be inserted consists of two solid compressible prosthesis elements as shown by FIG. 1, for example, the prosthesis element 140a (or 12 as designated in FIG. 1) is compressed and then placed in position. The compressible prosthesis element 140a can be compressed during the procedure using, for example, compression apparatus. Examples of compression apparatus that can be utilized to compress the prosthesis element 140a and insert it in the proper position are the pliers apparatus shown by FIGS. 34 and 35 and the thumbscrew apparatus shown by FIGS. 36 and 37, both described further below.

FIGS. 19 and 20 illustrate the use of pliers apparatus 150 to compress the prosthesis element 140a into a smaller cylindrical shape that is of a size that can be pushed through the portion 142 of the enlarged partially circular space 100 that intersects the additional spaces 110 and 110a. The compressible prosthesis element 140a is placed between the semi-cylindrical jaws 152a and 152b and compressed thereby. Thereafter, the lower end of the jaws 152a and 152b of the pliers apparatus 150 are inserted into the enlarged partially circular space 100 and a push rod 156 or the like is utilized to push the compressed prosthesis element 140a into the portion 142 of the enlarged partially circular space 100 that intersects the additional spaces 110a and 110b and in the additional spaces. Once in the portion 142, the compressed prosthesis element 140a expands to its original shape and into the additional spaces 110a and 110b.

FIGS. 21 and 22 illustrate placement of the prosthesis element 140a (e.g., the prosthesis element 12 as shown by FIG. 1) into the portion 142 using the inventive spinal disc insertion apparatus 30 shown by FIGS. 4-7. The open lower end 38 of the apparatus 30 is inserted into the enlarged partially circular space 100 between the adjacent vertebrae 82 and 84. The coring surface 54 of the lower end 38 of the shell 32 facilitates this process. Specifically, the sharp nature of the coring surface 54 cuts away any vertebrae material that otherwise might impede insertion of the shell 32 between the vertebrae. The plunger 60 is then utilized to push the compressed prosthesis element 140a into the portion of the enlarged partially circular space 100 that intersects the additional spaces 110a and 110b. Once in the portion 142, the compressed prosthesis element 140a expands to its original shape and into the additional spaces 110a and 110b.

If the prosthesis element 140a is to be formed in situ, the liquid or slurry material used to form the prosthesis element is injected or otherwise placed in the additional spaces 110a and 110b between the adjacent vertebrae 82 and 84 by way of the enlarged partially circular space 100 between the vertebrae. If a catalyst or second material is necessary to cause the liquid or slurry prosthesis element to harden, the catalyst or other material is then injected or otherwise placed in the additional spaces 110a and 110b and portion 142 and admixed with the base material. The base material (together with the catalyst or other material if a two-component system is used) essentially fills the additional spaces 110a and 110b and the portion 142 of the enlarged circular space 100 intersecting the same. The liquid or slurry prosthesis element 140a is then allowed to harden.

As shown by FIG. 23, the upper surfaces 116 of the additional spaces 110a and 110b prevent the expanded solid, compressible prosthesis element 140a or the hardened prosthesis element 140a formed in situ from coming out of the additional spaces. FIG. 24 is a partial back view of the adjacent vertebrae 82 and 84 showing the prosthesis element 140a in place within the additional spaces 110a and 110b.

Thereafter, the same process is repeated from the back and to the other side of the space 92 between the adjacent vertebrae 82 and 84 to place the second prosthesis element 140b between the adjacent vertebrae. As a preliminary step, the distractor 90 is removed. The prosthesis 140a keeps the vertebrae 82 and 84 spaced apart. The collar 96 is then put in position on the other side of the vertebrae 82 and 84 to facilitate the process. The specific steps described above are then carried out, that is, a second enlarged partially circular space is formed from the back and to the other side of the space 92 between the adjacent vertebrae 82 and 84 previously occupied by the degenerated disc 86 as shown by FIGS. 15 and 16. Additional spaces 110a and 110b are formed within the interiors of the adjacent vertebrae, each of the additional spaces intersecting the second enlarged partially circular space 100 and including an upper surface 116 adjacent to the second enlarged partially circular space as shown by FIGS. 17 and 18. As shown by FIGS. 19-22, the second prosthesis element 140b is then placed in the portion 142 of the second enlarged partially circular space 100 that intersects the additional spaces 110a and 110b and in the additional spaces whereby the upper surfaces 116 of the additional spaces prevent the second prosthesis element 140b from coming out of the additional spaces. Preferably, the same type of prosthesis element and same method used in connection with placing the prosthesis element 140a are used to place the prosthesis element 140b. For example, if the prosthesis element 140a is a solid, compressible prosthesis element such as the prosthesis element 12 shown by FIG. 1, the prosthesis element 140b is also a solid, compressible prosthesis element, such as the prosthesis element 14 shown by FIG. 1. If the spinal disc prosthesis insertion apparatus 30 is used to place the prosthesis element 140a, the spinal disc prosthesis insertion apparatus is used to place the prosthesis element 140b. Preferably, both the prosthesis element 140a and the prosthesis element 140b are pre-compressed and inserted into the shell 32 prior to the procedure.

FIG. 25 is a back view of the adjacent vertebrae 82 and 84 showing the prosthesis elements 140a and 140b after they have been placed in the portions 142 of the enlarged partially circular spaces 100 that intersect the additional spaces 110a and 110b and in the additional spaces. Once placed between the adjacent vertebrae 82 and 84, the two solid compressible prosthesis elements 140a and 140b will not come out of the additional spaces 110a and 110b within the interiors 112a and 112b of the adjacent vertebrae. The prosthesis elements 140a and 140b have long lives, e.g., when the elements are formed of polyurethane coated with "SILASTIC™," they have a useful life of twenty years or more. However, if and when it is necessary to remove and replace one or both of the prosthesis elements due to infection or the like or the lifespan of the prosthesis elements has been reached, the procedure required is very simple and cost efficient. That is, the vertebrae containing the prostheses are exposed and the prostheses are broken up using a drill bit and removed by way of the enlarged partially circular spaces between the adjacent vertebrae. Thereafter, new prosthesis elements are inserted in the additional spaces 110a and 110b within the interiors of the adjacent vertebrae as described above.

In a second embodiment of the inventive method, a spinal disc prosthesis including one or more solid prosthesis elements is placed between adjacent spinal vertebrae. The second embodiment of the inventive method is particularly suitable for use when bone resorption is an issue. For example, the second embodiment of the method can be used if biomechanical testing reveals that there would be too much bone resorption at the midline of the vertebral end-plates between the two side by side prosthesis elements described above due to changed pressure forces.

If it is known initially that the second embodiment of the inventive method will be utilized, the portions 86a, 86b and 86c of the degenerated disc 86 can be initially removed. Once the preliminary steps described above have been completed, the method is carried out. The steps of this embodiment of the method overlap to a large extent with the steps of the first embodiment of the method as described above. These overlapping steps will not be described in detail again. Except when indicated otherwise, the same options, steps and procedures apply.

Referring now again to FIGS. 15 and 16, as with the first embodiment of the method, a first enlarged partially circular space 100 is formed from the back and to one side of the space 92 between the adjacent vertebrae 82 and 84 previously occupied by the degenerated disc 86. Next, referring specifically to FIGS. 17 and 18, a first set of additional spaces 110a and 110b is formed within the interiors 112a and 112b of the adjacent vertebrae 82 and 84. Each of the additional spaces 110a and 110b of the first set intersects with the first enlarged partially circular space 100 and includes an upper surface 116 adjacent to the first enlarged partially circular space.

In the first embodiment of the inventive method, a prosthesis element is placed between the adjacent vertebrae 82 and 84 at this point. This is not the case in the second embodiment of the method. Rather, after the first enlarged partially circular space 100 and first set of additional spaces 110a and 110b are formed to one side of the space between the adjacent vertebrae 82 and 84, a second enlarged circular space 100 is formed from the back and to the other side of the space 92 between the adjacent vertebrae previously occupied by the degenerated disc. The same procedure, illustrated by FIGS. 15 and 16, is utilized to form the second enlarged partially circular space 100. Thereafter, as illustrated by FIGS. 17 and 18, a second set of additional spaces 110a and 110b are formed within the interiors 112a and 112b of the adjacent vertebrae 82 and 84. Each of the additional spaces 110a and 110b of the second set intersects the second partially enlarged space 100 and includes an upper surface 116 adjacent to the second partially circular enlarged space. FIG. 26 illustrates the first and second enlarged partially circular spaces 100 formed from the back and to the two sides of the space 92 between the adjacent vertebrae 82 and 84 previously occupied by the degenerated disc, and the first and second sets of additional spaces 110a and 110b within the interiors 112a and 112b of the adjacent vertebrae as described above.

Next, referring to FIGS. 26-29, the first set of additional spaces 110a and 110b, the second set of additional spaces 110a and 110b and the portions 142 of the first and second enlarged partially circular spaces 100 that intersect the respective additional spaces are interconnected to form an enlarged disc cavity 160 within the interiors 162 of the adjacent vertebrae 82 and 84. The enlarged disc cavity includes an upper surface 164 between the first and second enlarged partially circular spaces 100 and the upper surfaces 116 of the first and second sets of additional spaces 110a and 110b.

As best shown by FIG. 28, prior to interconnecting the spaces, bone nubbins 170 separate the first set of additional spaces 110*a* and 110*b*, the second set of additional spaces 110*a* and 110*b* and the portions 142 of the first and second enlarged partially circular spaces 100 that intersect the respective additional spaces. The spaces are interconnected by removing the bone nubbins 170 between the spaces.

The bone nubbins 170 can be removed from between the spaces using a rasp 180 specially constructed in accordance with the invention. The rasp 180 is best shown by FIGS. 12 and 13. It includes an elongated shaft 182 and a file portion 184 attached to the shaft and transversely extending therefrom. The file portion 184 preferably extends substantially perpendicularly from the elongated shaft 182, most preferably at a 90 degree angle from the elongated shaft. The file portion 184 of the rasp 180 includes an outside surface 186 having a plurality of filing ridges 188 thereon. The shaft 182 and the file portion 184 each have a cylindrical cross-section (each having a diameter of about 6 mm). The elongated shaft 182 of the rasp 180 is preferably about 18 cm long. The file portion 184 is preferably about 15 mm long.

Prior to interconnecting the spaces, any of the degenerated disc 86 remaining between the adjacent vertebrae and between the enlarged partially circular spaces 100 (the portion 86*c* shown by FIG. 14) is removed. Next, the rasp 180 is inserted into one of the enlarged partially circular spaces 100 such that the file portion 184 of the rasp is below the upper surface 116 of the additional space 110*a* or 110*b*. The rasp 180 is then placed by feel against the bone nubbins and moved up and down and back and forth at depth within the interiors of the adjacent vertebrae to remove the bone nubbins 170. Care is taken to rasp only the bone nubbins separating the first and second sets of additional spaces 110*a* and 110*b* and the portions 142 of the first and second enlarged partially circular spaces 100 that intersect the respective additional spaces; i.e., care is taken not to remove the upper surfaces 164 and 116 of the enlarged disc cavity 160. FIG. 29 illustrates the enlarged disc cavity 160 after the bone nubbins 170 have been removed to form the enlarged disc cavity 160.

Next, a solid prosthesis element 200 is placed within the enlarged disc cavity 160. The upper surfaces 164 and 116 of the enlarged disc cavity prevent the prosthesis element 200 from coming out of the first and second enlarged partially circular spaces 100. In one embodiment, a single solid compressible prosthesis element of a size sufficient to essentially fill the enlarged disc cavity 160, such as the prosthesis element 18 shown by FIG. 2, is utilized. In another embodiment, two solid compressible prosthesis elements that together are of a size sufficient to fill the enlarged disc cavity 160, such as the prosthesis elements 20 and 22 shown by FIG. 3, are utilized. The compressible prosthesis element or elements can be compressed during the procedure using, for example, compression apparatus specially constructed in accordance with the invention (such as the pliers apparatus or thumbscrew apparatus described below). Alternatively, the compressible prosthesis element or elements can be put into place using the inventive spinal prosthesis insertion apparatus 30, as illustrated by FIG. 30. For example, when one or more compressible prosthesis elements are utilized, the compressed element or elements are pushed into the enlarged disc cavity 160 by way of one of the enlarged partially circular spaces 100 formed between the adjacent vertebrae 82 and 84. Once in the enlarged disc cavity 160, the compressed element or elements expand to fill the cavity.

As with the first embodiment of the inventive method, a single prosthesis element or two or more prosthesis elements 200 can be formed in the enlarged disc cavity 160 in situ. For example, as shown by FIG. 31, the liquid or slurry material used to form the prosthesis element can be injected into the enlarged disc cavity 160 by way of one of the enlarged partially circular spaces 100 with a syringe 205. Enough material is used (including the catalyst or other second material if a two-component system is utilized) to fill the entire enlarged disc cavity 160. The material is then caused or allowed to harden as discussed above.

FIG. 32 is a back view of the adjacent vertebrae 82 and 84 showing the enlarged disc cavity 160 having a single prosthesis element 200 therein (such as the prosthesis element 18 shown by FIG. 2), after the prosthesis element has been allowed to expand within the cavity (if the prosthesis element is a solid, compressible prosthesis element) or harden in the cavity (if the element was formed in situ). FIG. 33 is a back view of the adjacent vertebrae 82 and 84 showing the enlarged disc cavity 160 having two compressible prosthesis elements 200 (such as the elements 20 and 22 shown by FIG. 3) expanded therein.

The upper surfaces of the enlarged disc cavity 160 prevent the expanded solid, compressible prosthesis element(s) 200 or the hardened prosthesis element 200 formed in situ from coming out of the additional spaces. The prosthesis element (s) are trapped in the enlarged disc cavity 160 and function in the same manner as a normal vertebra disc. The enlarged disc cavity 160 provides a broader surface of contact to the prosthesis and allows for less vertebral bone resorption. Less pressure is applied against the prosthesis element(s) at any given point which makes the prosthesis element(s) more stable in place, less likely to dislodge, more resistant to abrasion and less susceptible to resorption of bone pushing against the element(s) over time. As with the prosthesis elements 140*a* and 140*b*, the prosthesis element(s) 200 have long lives, but if necessary can be easily removed and replaced by way of one or both of the enlarged partially circular spaces.

Figure 34:
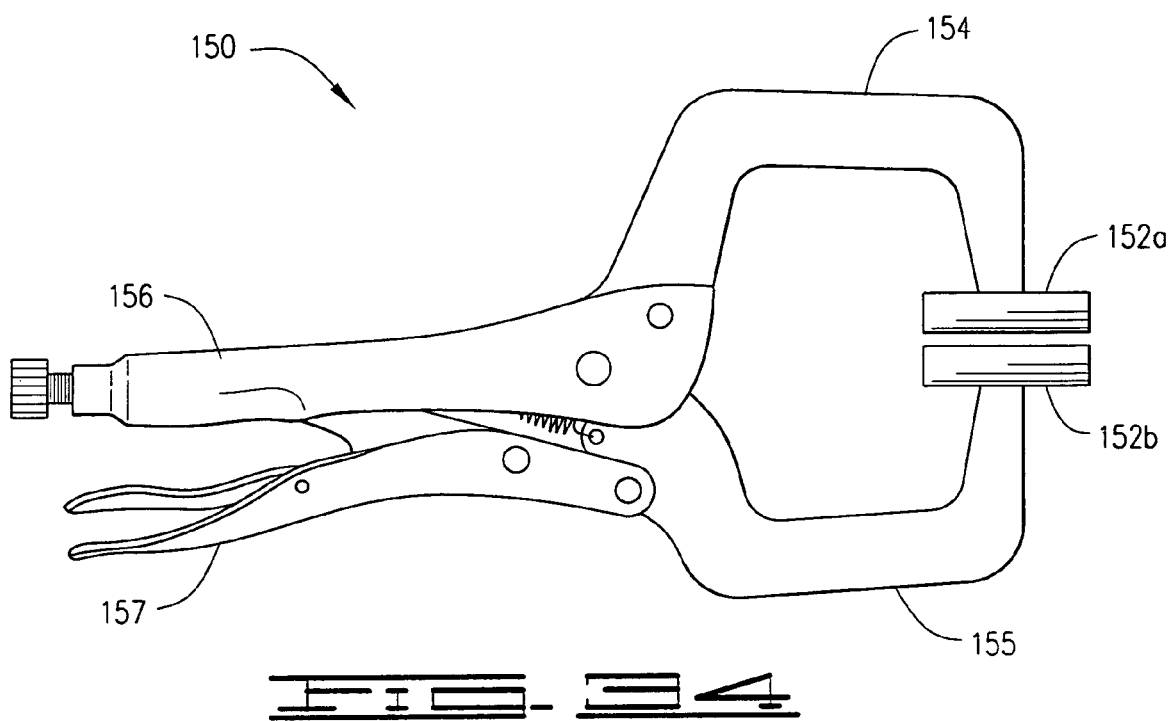
FIG. 34 is a side view of the inventive pliers apparatus
Figure 35:
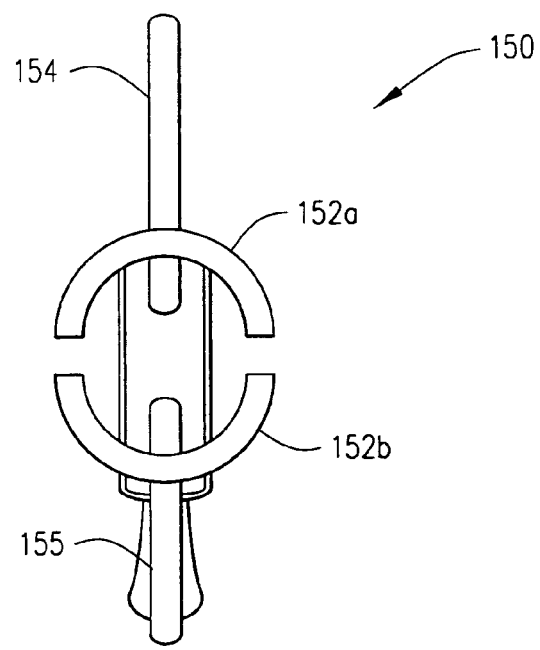
FIG. 35 is a front view of the pliers apparatus of FIG. 34.

FIGS. 34 and 35 illustrate the pliers apparatus 150 that can be utilized to compress a solid, compressible prosthesis element and insert the element between adjacent spinal vertebrae in accordance with either embodiment of the method described above. As shown, the pliers 150 are similar to similar vice-grip pliers except that the jaws 152*a* and 152*b* are semi-cylindrical for compressing the solid compressible prosthesis element. The jaws 152*a* and 152*b* are positioned adjacent to each other by movable arms 154 and 155 connected thereto that open and close the jaws. The arms 154 and 155 are in turn connected to the handles 156 and 157 of the pliers 150. The inside surfaces of the jaws 152*a* and 152*b* are preferably coated with "TEFLON™," to facilitate pushing a compressed disc prosthesis out of the closed jaws.

Figure 36:
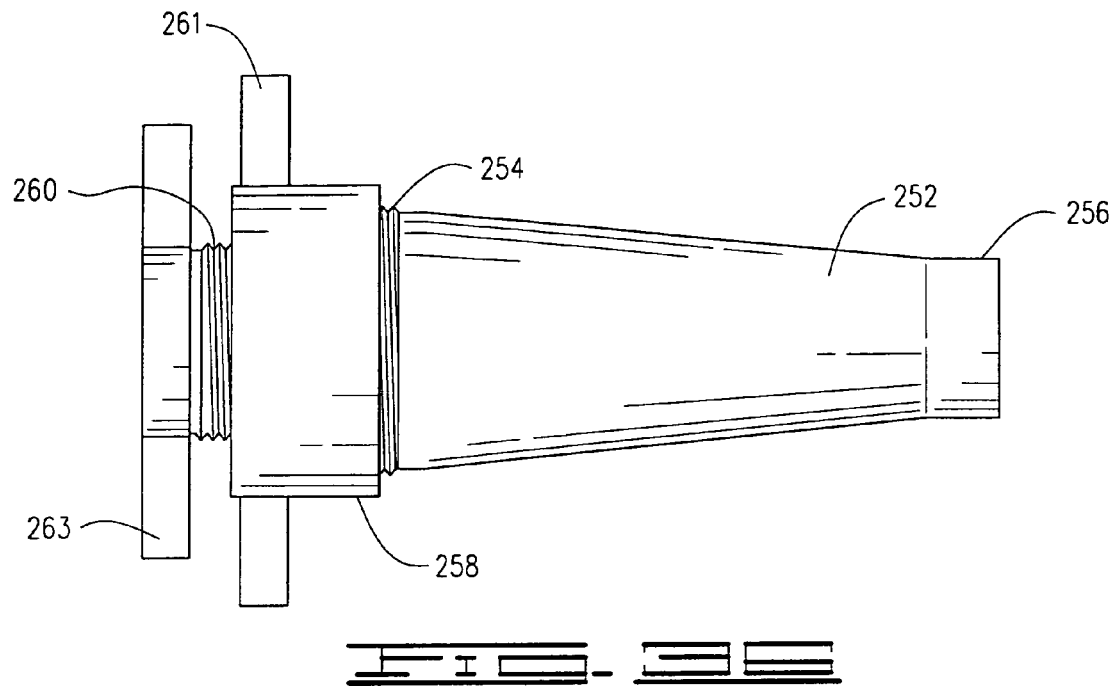
FIG. 36 is a side view of the inventive thumbscrew apparatus.
Figure 37:
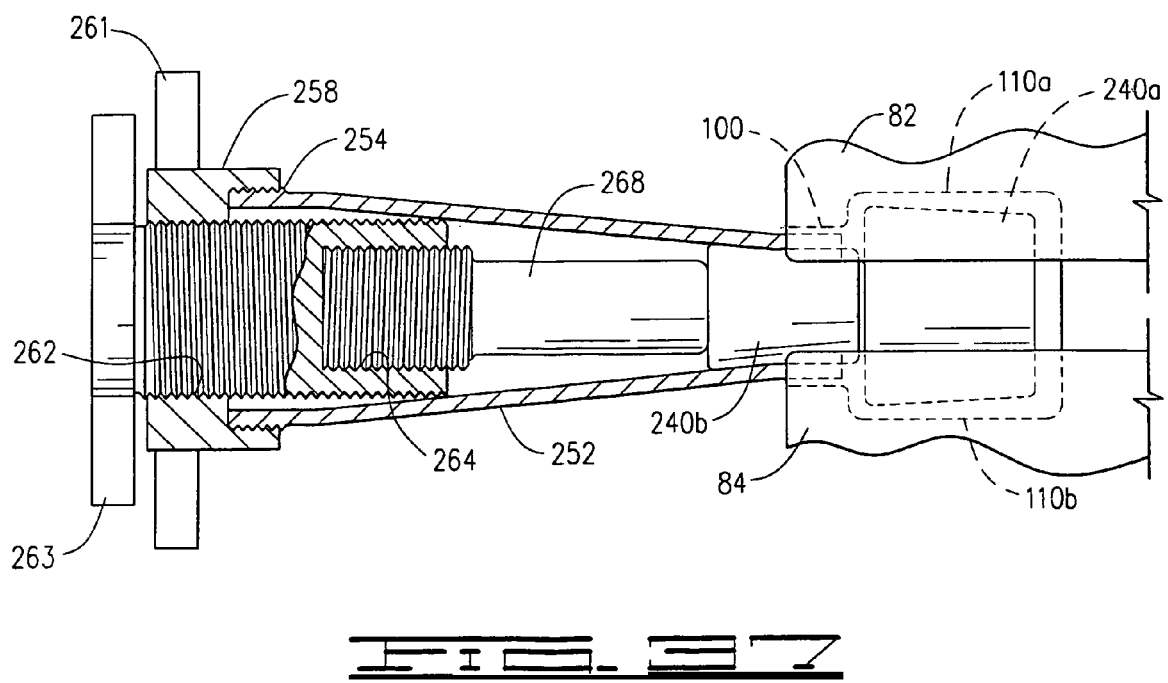
FIG. 37 is a side cutaway view of the thumbscrew apparatus illustrating its use whereby a compressible prosthesis element is placed in position within the interiors of adjacent vertebrae.

FIGS. 36 and 37 illustrate a thumbscrew apparatus 250 that can be utilized to compress one or more solid, compressible prosthesis elements and insert the element(s) between adjacent spinal vertebrae in accordance with either embodiment of the method described above. As shown, the thumbscrew apparatus 250 compresses solid compressible prosthesis elements 240*a* and 240*b* into small cylindrical shapes and pushes them through the enlarged partially circular opening 100 into the additional spaces 110*a* and 110*b* formed in the adjacent vertebrae 82 and 84. The thumbscrew apparatus 250 comprises an elongated tapered tube 252 having an externally threaded non-tapered large end 254 and a smooth non-tapered small end 256. The small end 256 is of a size that fits within the enlarged partially circular space 100 formed in the upper and lower vertebrae 82 and 84 as described above. An internally threaded cap 258 is threaded onto the externally threaded non-tapered large end 254 of the tapered tube 252, and an elongated threaded thumbscrew 260 is threaded into an internally threaded smaller opening 262 in the cap 258.

The cap 258 and the thumbscrew 260 each include a pair of opposed handles 261 and 263, respectively, for turning the cap and thumbscrew.

The elongated threaded thumbscrew 260 includes an internally threaded counterbore 264 at its end within the tapered tube 252. Various sizes of push rods can be threaded into the thumbscrew 260 as required. As shown, two solid compressible prosthesis elements 240a and 240b are utilized in the thumbscrew apparatus 250 to place the element 240a in the portion 142 of the enlarged partially circular opening 100 and in the additional spaces 110a and 110b formed in one side of the adjacent vertebrae 82 and 84. The small end of the tube 252 of the thumbscrew apparatus 250 is inserted into position between the adjacent vertebrae 82 and 84 and the compressible prosthesis elements 240a and 240b are moved forwardly until the element 240a is pushed into position using the push rod 68.

Thus, the present invention is well adapted to obtain the objects and advantages mentioned as well as those which are inherent therein. While numerous changes may be made by those skilled in the art, such changes are encompassed within the spirit of this invention as defined by the appended claims.

What is claimed is:

1. A method of placing a spinal disc prosthesis including two solid prosthesis elements between adjacent spinal vertebrae comprising the steps of:
   (a) forming an enlarged partially circular space from the back and to one side of the space between adjacent vertebrae previously occupied by a degenerated disc;
   (b) forming additional spaces within the interiors of the adjacent vertebrae, each of said additional spaces intersecting said enlarged partially circular space and including an upper surface adjacent to said enlarged partially circular space;
   (c) injecting a liquid or slurry material into said enlarged partially circular space and said additional spaces and causing or allowing said material to harden therein to produce a solid prosthesis element whereby said upper surfaces of said additional spaces prevent said prosthesis element from coming out of said additional spaces; and
   (d) repeating steps (a), (b) and (c) from the back and to the other side of the space between adjacent vertebrae.

2. The method of claim 1 further comprising the step of injecting a catalyst into said enlarged partially circular space and said additional spaces to cause said liquid or slurry material to harden.

3. The method of claim 1 wherein said additional spaces within the interiors of the adjacent vertebrae are vertically aligned.

4. The method of claim 1 wherein the enlarged partially circular space between the adjacent spinal vertebrae is formed using a drill bit.

5. The method of claim 1 wherein the additional spaces within the interiors of the adjacent vertebrae are formed using a router.

6. The method of claim 5 wherein said router comprises:
   (a) an enlarged cylindrical portion of a size sufficient to form said additional spaces and having a diameter equal to or slightly less than the diameter of said enlarged partially circular space, said enlarged cylindrical portion including a flat upper surface, a flat lower surface and a cylindrical body connecting said upper surface to said lower surface, said cylindrical body including a plurality of sharp cutting points on the outside surface thereof for forming said additional spaces; and
   (b) a cylindrical shaft extending outwardly from said upper surface of said enlarged cylindrical portion, said shaft having a diameter substantially less than the diameter of said enlarged cylindrical portion.

7. A method of placing a spinal disc prosthesis including one or more solid prosthesis elements between adjacent spinal vertebrae comprising the steps of:
   (a) forming a first enlarged partially circular space from the back and to one side of the space between adjacent vertebrae previously occupied by a degenerated disc;
   (b) forming a first set of additional spaces within the interiors of the adjacent vertebrae, each of said additional spaces of said first set intersecting said first enlarged partially circular space and including an upper surface adjacent to said first enlarged partially circular space;
   (c) forming a second enlarged partially circular space from the back and to the other side of the space between the adjacent vertebrae previously occupied by the degenerated disc;
   (d) forming a second set of additional spaces within the interiors of the adjacent vertebrae, each of said additional spaces of said second set intersecting said second partially circular enlarged space and including an upper surface adjacent to said second partially circular enlarged space;
   (e) interconnecting said first set of additional spaces, said second set of additional spaces and the portions of said first and second enlarged partially circular spaces that intersect the respective additional spaces to form an enlarged disc cavity within the interiors of the adjacent vertebrae, said enlarged disc cavity including an upper surface between said first and second enlarged partially circular spaces and said upper cavities of said first and second sets of additional spaces; and
   (f) placing a solid prosthesis element in said enlarged disc cavity whereby said upper surfaces of said enlarged disc cavity prevent said prosthesis element from coming out of said first and second enlarged partially circular spaces.

8. The method of claim 7 wherein said solid prosthesis element is placed in said enlarged disc cavity in accordance with step (f) by placing a compressed, solid, compressible prosthesis element into said enlarged disc cavity through one of said first and second enlarged partially circular spaces and allowing said compressed prosthesis element to expand into said enlarged disc cavity.

9. The method of claim 8 wherein said compressed, solid, compressible prosthesis element is placed into said enlarged disc cavity through one of said first and second enlarged partially circular spaces by compressing said prosthesis element with a compression apparatus and pushing said prosthesis element from said compression apparatus though one of said first and second enlarged partially circular spaces into said enlarged disc cavity.

10. The method of claim 8 wherein said compressed, solid, compressible prosthesis element is placed into said enlarged disc cavity through one of said first and second enlarged partially circular spaces by compressing said element and placing said element in an insertion shell, and then pushing said element from said insertion shell into said enlarged disc cavity.

11. The method of claim 10 wherein said prosthesis element is compressed and placed in said insertion shell at a location remote from the location where said method of placing the disc prosthesis between adjacent spinal vertebrae is carried out.

12. The method of claim 7 wherein said solid prosthesis element is placed in said enlarged disc cavity in accordance with step (f) by placing two compressed, solid, compressible prosthesis elements into said enlarged disc cavity and allowing each element to expand therein, each of said compressed, solid, compressible prosthesis elements being placed in said enlarged disc cavity through one of said first and second enlarged partially circular spaces.

13. The method of claim 7 wherein said prosthesis element(s) have an oval cross-section.

14. The method of claim 7 wherein said solid prosthesis element is placed in said enlarged disc cavity in accordance with step (f) by injecting a liquid or slurry form of said prosthesis element into said enlarged disc cavity and causing or allowing said prosthesis element to harden therein.

15. The method of claim 14 further comprising the step of injecting a catalyst into said enlarged disc cavity after said liquid or slurry form of said prosthesis element is injected therein to cause said prosthesis element to harden.

16. The method of claim 7 wherein said first and second enlarged partially circular spaces between the adjacent spinal vertebrae is formed using a drill bit.

17. The method of claim 7 wherein the additional spaces within the interiors of the adjacent vertebrae are formed using a router.

18. The method of claim 17 wherein said router comprises:
(a) an enlarged cylindrical portion of a size sufficient to form said additional spaces and having a diameter equal to or slightly less than the diameter of said enlarged partially circular space, said enlarged cylindrical portion including a flat upper surface, a flat lower surface and a cylindrical body connecting said upper surface to said lower surface, said cylindrical body including a plurality of sharp cutting points on the outside surface thereof for forming said additional spaces; and
(b) a cylindrical shaft extending outwardly from said upper surface of said enlarged cylindrical portion, said shaft having a diameter substantially less than the diameter of said enlarged cylindrical portion.

19. The method of claim 7 wherein said first set of additional spaces, said second set of additional spaces and the portions of said first and second enlarged partially circular spaces that intersect the respective additional spaces are interconnected in step (e) by removing bone nubbins between the first set of additional spaces and the portion of the first enlarged space that intersects the same and the second set of additional spaces and the portion of the second enlarged space that intersects the same.

20. The method of claim 19 wherein said bone nubbins are removed with a rasp comprising an elongated shaft and a file portion attached to said shaft and transversely extending therefrom.

21. A method of placing a spinal disc prosthesis including two solid prosthesis elements between adjacent spinal vertebrae comprising the steps of:
(a) forming an enlarged partially circular space from the back and to one side of the space between adjacent vertebrae previously occupied by a degenerated disc;
(b) forming additional spaces within the interiors of the adjacent vertebrae, each of said additional spaces intersecting said enlarged partially circular space and including an upper surface adjacent to said enlarged partially circular space;
(c) placing a compressed, solid, compressible prosthesis element in said portion of said enlarged partially circular space that intersects said additional spaces and allowing said compressed prosthesis element to expand in said additional spaces whereby said upper surfaces of said additional spaces prevent said prosthesis element from coming out of said additional spaces; and
(d) repeating steps (a), (b) and (c) from the back and to the other side of the space between adjacent vertebrae.

22. The method of claim 21 wherein said compressed, solid, compressible prosthesis element is placed in said portion of said enlarged partially circular space that intersects said additional spaces by compressing said prosthesis element with a compression apparatus and pushing said prosthesis element from said compression apparatus into said portion of said enlarged partially circular space that intersects said additional spaces.

23. The method of claim 22 wherein said compression apparatus is pliers apparatus or a thumbscrew apparatus.

24. The method of claim 21 wherein said compressed, solid, compressible prosthesis element is placed in said portion of said enlarged partially circular space that intersects said additional spaces by compressing said element and placing said element in an insertion shell, and then pushing said element from said insertion shell into said portion of said enlarged partially circular space that intersects said additional spaces.

25. The method of claim 24 wherein said prosthesis element is compressed and placed in said insertion shell at a location remote from the location where said method of placing the disc prosthesis between adjacent spinal vertebrae is carried out.

26. The method of claim 24 wherein said prosthesis element has a circular cross-section.

27. The method of claim 24 wherein said prosthesis element and said insertion shell each have a circular cross-section.

* * * * *